US011832631B2

(12) United States Patent
Ben-Zvi et al.

(10) Patent No.: US 11,832,631 B2
(45) Date of Patent: *Dec. 5, 2023

(54) OIL SUSPENSIONS OF EDIBLE SOLIDS, TRIGLYCERIDES WITH SATURATED FATTY ACIDS, MCT OILS WITH ANTIOXIDANTS AND SOLID AND SEMI-SOLID OIL-DERIVATIVES FOR FOOD

(71) Applicant: Omega 3 Galilee Ltd., Misgav (IL)

(72) Inventors: Guy Ben-Zvi, Misgav (IL); Alisa Dunkel, Kermiel (IL)

(73) Assignee: Omega 3 Galilee Ltd., Misgav (IL)

( * ) Notice: Subject to any disclaimer, the term of this patent is extended or adjusted under 35 U.S.C. 154(b) by 27 days.

This patent is subject to a terminal disclaimer.

(21) Appl. No.: 17/570,770

(22) Filed: Jan. 7, 2022

(65) Prior Publication Data

US 2022/0125066 A1 Apr. 28, 2022

Related U.S. Application Data

(63) Continuation of application No. 17/564,223, filed on Dec. 29, 2021, which is a continuation-in-part of application No. PCT/IL2020/050787, filed on Jul. 14, 2020.

(60) Provisional application No. 63/270,899, filed on Oct. 22, 2021, provisional application No. 63/256,661, filed on Oct. 18, 2021, provisional application No. 63/254,701, filed on Oct. 12, 2021.

(30) Foreign Application Priority Data

Aug. 4, 2019 (IL) .......................................... 268457

(51) Int. Cl.
A23D 9/007 (2006.01)
A23D 9/04 (2006.01)
A23D 9/06 (2006.01)
A61K 9/10 (2006.01)

(52) U.S. Cl.
CPC ............... *A23D 9/007* (2013.01); *A23D 9/04* (2013.01); *A23D 9/06* (2013.01); *A61K 9/10* (2013.01)

(58) Field of Classification Search
CPC ............. A23D 9/04; A23D 9/007; A23D 9/06
See application file for complete search history.

(56) References Cited

U.S. PATENT DOCUMENTS

| 5,326,582 A * | 7/1994 | Hair ....................... A23D 9/007 426/442 |
| 5,518,744 A * | 5/1996 | Kaeser ................... B65D 85/72 426/94 |
| 5,958,499 A * | 9/1999 | Desai ...................... A23L 25/30 426/612 |
| 6,048,557 A | 4/2000 | Van Den Burg et al. |
| 7,947,656 B2 | 5/2011 | Yamasaki et al. |
| 8,197,851 B2 * | 6/2012 | Bos ........................ A23D 9/007 424/489 |
| 2003/0185877 A1 | 10/2003 | Betz et al. |
| 2005/0025872 A1 * | 2/2005 | Joseph .................... A23D 7/011 426/601 |
| 2008/0026109 A1 | 1/2008 | Abril |
| 2010/0196534 A1 * | 8/2010 | Illingworth ......... A23L 27/2026 426/585 |
| 2012/0207800 A1 | 8/2012 | Abu-Backer et al. |
| 2013/0156892 A1 | 6/2013 | Mussawir-Key |
| 2014/0134092 A1 * | 5/2014 | Shankman ............ C01B 32/184 423/448 |
| 2019/0174792 A1 | 6/2019 | Abu-Hadran et al. |
| 2019/0373925 A1 | 12/2019 | Higuchi et al. |

FOREIGN PATENT DOCUMENTS

| CN | 104394850 A | 3/2015 |
| EP | 1505878 | 2/2005 |
| JP | H0779700 | 3/1995 |
| JP | H01-023849 | 1/2001 |

(Continued)

OTHER PUBLICATIONS

"About Palm Oil," Palm Oil World website, https://web.archive.org/web/ 20130126125250/http://www.palmoilworld.org/about_palmoil.html, archived on Jan. 26, 2013 (Year: 2013).*
International Search Report for PCT application No. PCT/IL2020/050787 dated Sep. 8, 2020.
Paine et al; Means for Preventing "Explosive" or Bursting Fermentation of Chocolate-Coated Fondant Candy; Industrial and Engineering Chemistry; vol. 19, No. 3, Mar. 1927.
Dos Santos, Luana Cristina et al; Flow properties of coarse and fine sugar powders; Wiley Journal of Food Process Engineering; Oct. 24, 2017.
Büschgens Christoph et al; Assessment of dust explosions in the sugar industry with regard to screening technology; Technology; Sugar Industry 142 (2017) No. 7, 2017.

(Continued)

Primary Examiner — Jeffrey P Mornhinweg
(74) Attorney, Agent, or Firm — PEARL COHEN ZEDEK LATZER BARATZ LLP

(57) ABSTRACT

Taste-enhanced liquid, semi-solid and/or solid oil-based suspensions are provided, which consist of a carrier oil and edible solid particles (e.g., crystalline salt and/or sugar, and optionally spices) having median diameter of less than 15 μm. The particles are reduced in size in the suspension, allowing enhancement of their organoleptic effects while reducing their amount to meet nutritional demands. The solid or semi-solid oil-derivatives comprise heterogeneous triglycerides of saturated fatty acids, including at least one saturated fatty acid having 12 carbons or more—selected to provide a required temperature-viscosity profile and/or a required melting temperature profile of the oil-derivative that corresponds to the food product. Also, non-oxidizing frying oil is provided, based on saturated fatty acids. The frying oil comprises triglycerides that include mostly or wholly saturated fatty acids, as well as small amounts of antioxidants that prevent residual oxidation of the oil during prolonged frying.

10 Claims, 14 Drawing Sheets

(56) References Cited

FOREIGN PATENT DOCUMENTS

| | | |
|---|---|---|
| JP | 2004500392 | 1/2004 |
| JP | 2006502127 | 1/2006 |
| JP | 2008541713 | 11/2008 |
| JP | 2013522233 | 6/2013 |
| JP | 2019517800 | 6/2019 |
| JP | 2019172995 | 10/2019 |
| WO | WO2006/011479 | 2/2006 |
| WO | WO2008/003064 | 1/2008 |
| WO | WO2016007026 | 1/2016 |
| WO | WO 2017/207686 A1 * | 7/2017 ............... A23G 1/30 |
| WO | WO2018155488 | 2/2019 |
| WO | WO2020167690 | 8/2020 |

OTHER PUBLICATIONS

Di Benedetto A. et al; Modelling the effect of particle size on dust explosions; Chemical Engineering Science 65 (2010), 772-779; Sep. 30, 2009.

Jiang Juju et al; Study of Parameters and Theory of Sucrose Dust Explosion; Energies 2022; https://www.mdpi.com/journal/energies; Feb. 16, 2022, MDPI.

Bratu Magda Gabriela et al; The Influence of Additives on Preparing the Fondant; The Annals of "Valahia" University of Târgoviçte Fascicle VIII; 2007.

Bück Andreas et al; Model-based control of particle properties in fluidised bed spray granulation; Powder Technology 270 (2015) 575-583; Jul. 26, 2014.

Cuq B. et al; Agglomeration/granulation in food powder production; Woodhead Publishing Limited, 2013.

Office Action for CN Application No. 2020800523826 dated Nov. 7, 2022.

Teramukai, Kazuyoshi, et al. "Effective extraction of carotenoids from brown seaweeds and vegetable leaves with edible oils." Innovative Food Science & Emerging Technologies 60 (2020): 102302. Kazuo Miyashita et al. Mar. 31, 2020 (Mar. 31, 2020) the whole document 1-60.

A Hategekimana, Joseph, et al. "Vitamin E nanoemulsions by emulsion phase inversion: Effect of environmental stress and long-term storage on stability and degradation in different carrier oil types." Colloids and Surfaces A: Physicochemical and Engineering Aspects 483 (2015): 70-80. Fang Zhong et al. Oct. 20, 2015 (Oct. 20, 2015) the whole document 1-60.

Han, Si-fei, et al. "Lipid-based formulations to enhance oral bioavailability of the poorly watersoluble drug anethol trithione: effects of lipid composition and formulation." International journal of pharmaceutics 379.1 (2009): 18-24. Han si fei et al. Sep. 8, 2009 (Sep. 8, 2009) the whole document.

International Search Report for PCT Application No. PCT/IL2022/051004 dated Dec. 15, 2022.

Examination report for SG Application No. 11202200586Y dated Sep. 14, 2023.

* cited by examiner

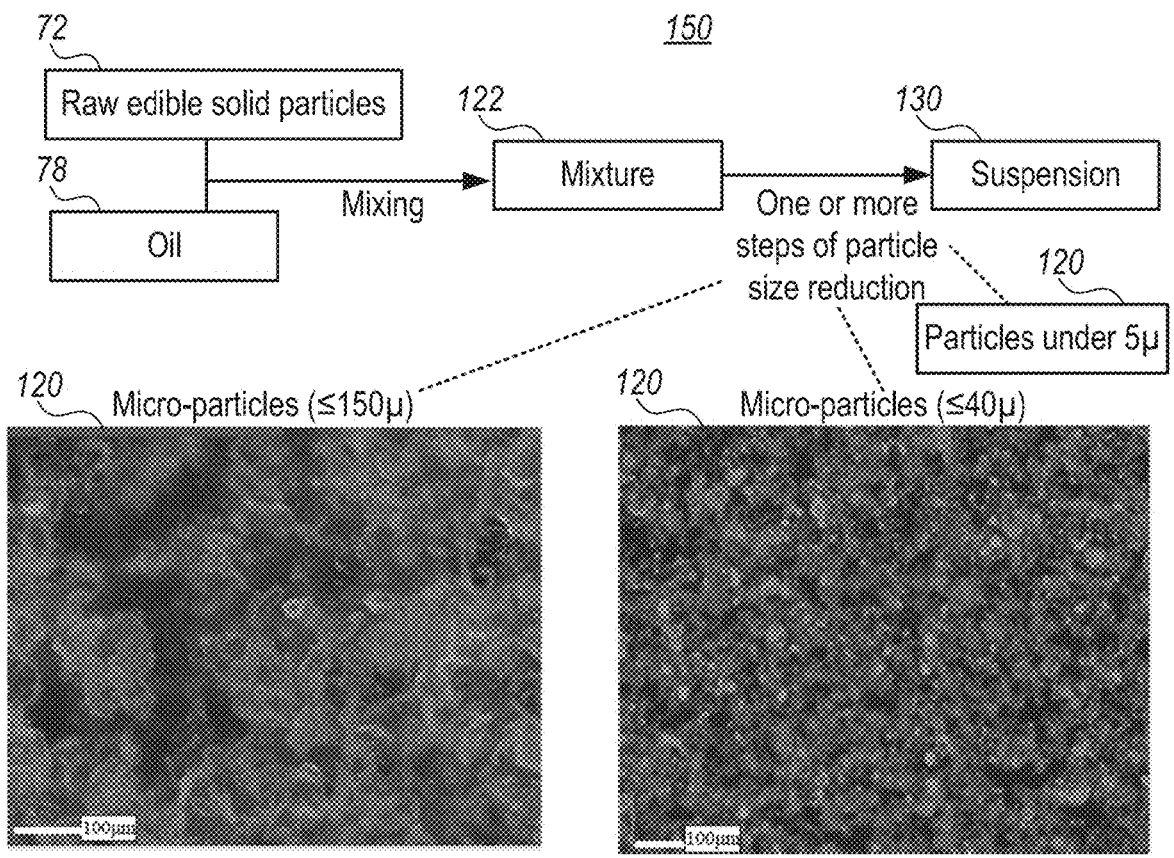
Figure 1
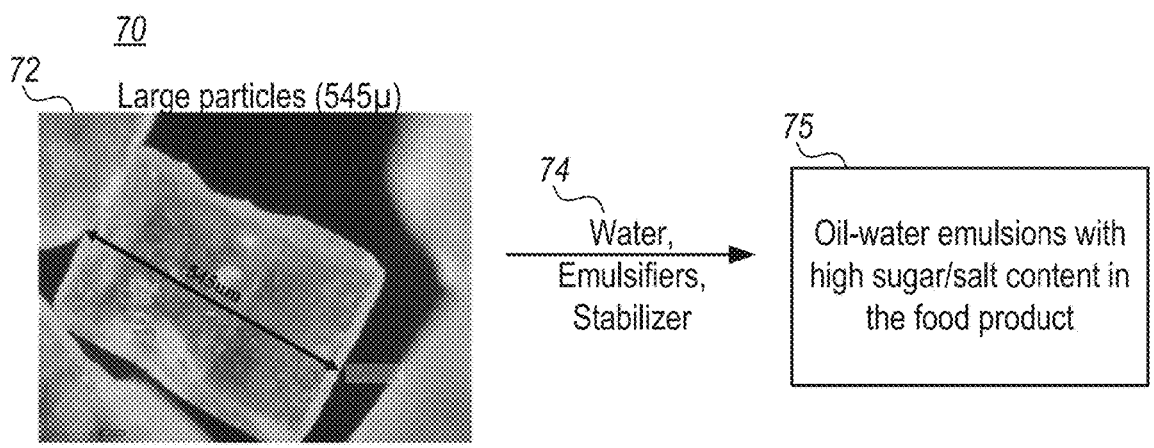
Figure 2 – Prior art

Figure 5A
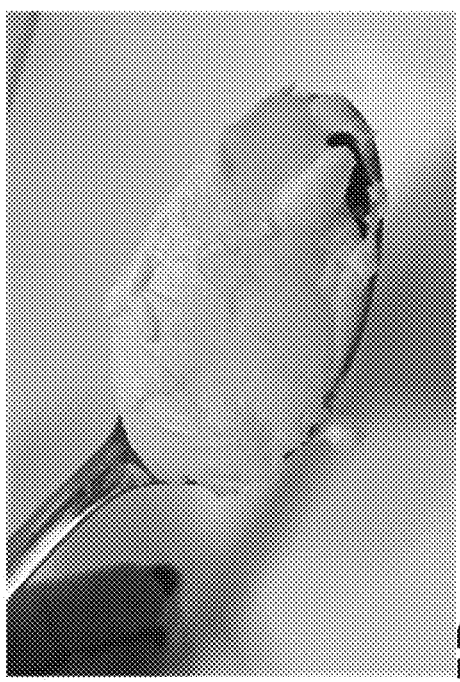
Figure 5B
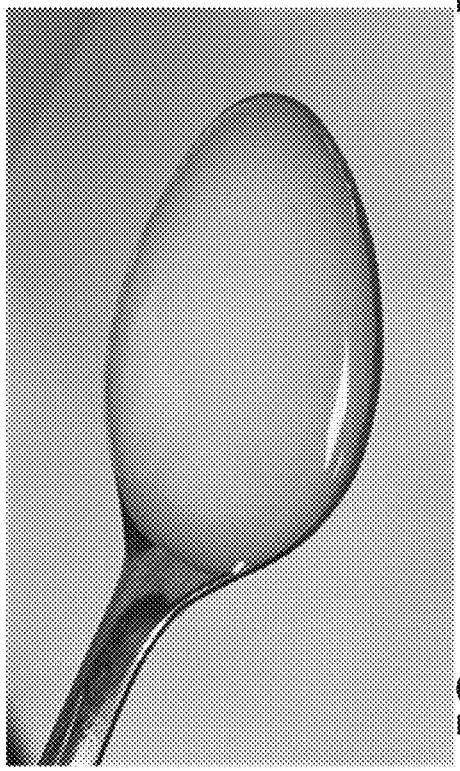
Figure 5C
Figure 5D

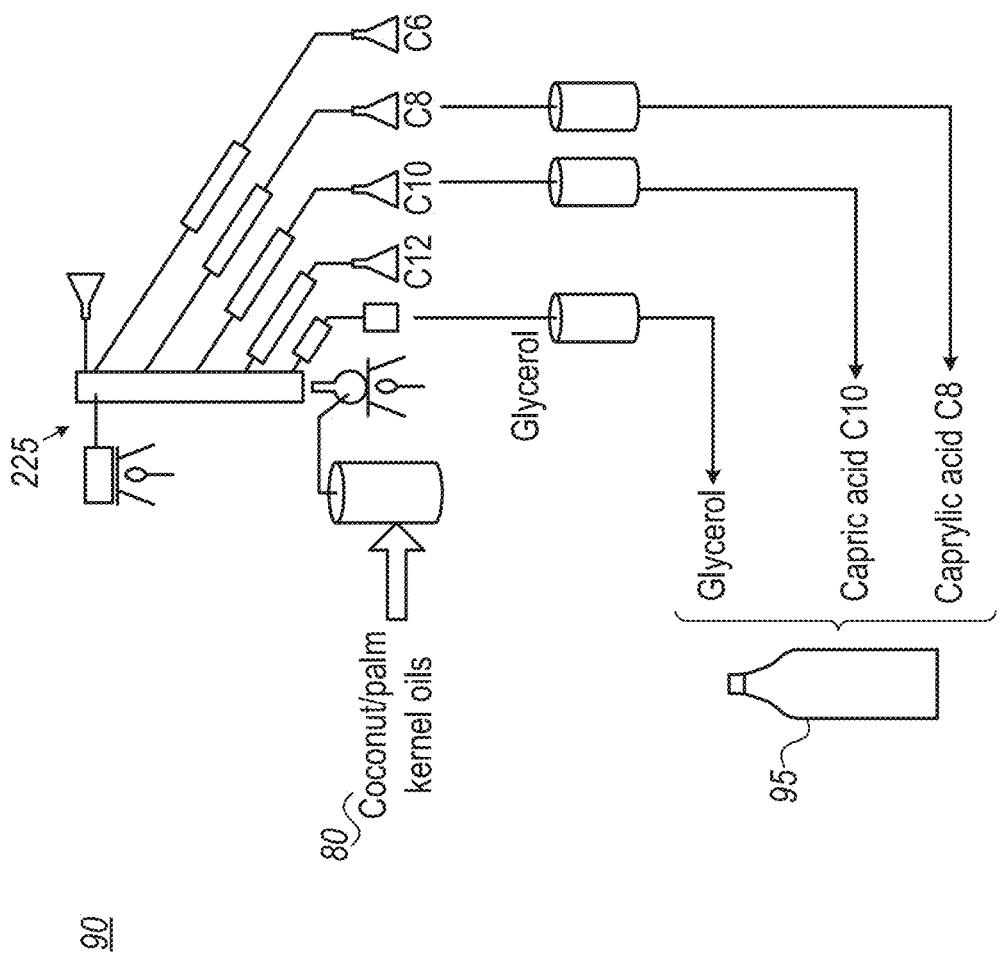
Figure 6A – Prior art

200

| | |
|---|---|
| 205 | Preparing a solid or semi-solid oil-derivative for a food product |
| 210 | Defining a required temperature-viscosity profile and/or a required melting temperature profile of the solid or semi-solid oil derivative |
| 220 | Deriving a required profile of triglycerides with saturated fatty acids in the solid or semi-solid oil-derivative to yield the required temperature-viscosity profile and/or a required melting temperature profile |
| 225 | Heat distillation and fractionation of raw vegetable oil |
| 230 | Re-esterifying the required profile of saturated fatty acids from the distilled components and optionally from an external source, to yield the oil derivative |
| 240 | Including in the solid or semi-solid oil derivative at least one saturated fatty acid with 12 carbons or more, optionally in addition to caprylic and capric acids |
| 242 | Selecting the additional saturated fatty acid(s) as viscosity and/or melting temperature modifier(s) |
| 244 | Using lauric acid from the distilled components in addition to caprylic and capric acids |
| 246 | Using myristic, palmitic and/or stearic acids from an external source in addition to caprylic and capric acids |
| 250 | Adding at least one edible solid as organoleptic modifier to the solid or semi-solid oil derivative |

*Figure 8*

OIL SUSPENSIONS OF EDIBLE SOLIDS, TRIGLYCERIDES WITH SATURATED FATTY ACIDS, MCT OILS WITH ANTIOXIDANTS AND SOLID AND SEMI-SOLID OIL-DERIVATIVES FOR FOOD

CROSS REFERENCE TO RELATED APPLICATIONS

This application is a Continuation of U.S. application Ser. No. 17/564,223 filed on Dec. 29, 2021 which is a Continuation-In-Part of WIPO Application No. PCT/IL2020/050787 filed on Jul. 14, 2020, claiming priority from Israeli Application No. 268457 filed on Aug. 4, 2019. This application further claims priority from U.S. Provisional Application No. 63/254,701 filed on Oct. 12, 2021, from U.S. Provisional Application No. 63/256,661 filed on Oct. 18, 2021, and from U.S. Provisional Application No. 63/270,899 filed on Oct. 22, 2021, which are incorporated herein by reference in their entirety.

BACKGROUND OF THE INVENTION

1. Technical Field

The present invention relates to the field of food engineering, in particular in relation to oils and fats for the food industry, and more particularly, to oils with microparticles of edible solids, edible solids, triglycerides with saturated fatty acids, MCT oils with antioxidants and solid and semi-solid oil-derivatives for food applications.

2. Discussion of Related Art

Sweetened or salted foods currently include large amounts of sugar or salt, and typically require using water-based emulsions, emulsifiers and stabilizers to support these large amounts of sugar or salt, especially in oil-based products.

Vegetable oils comprise mixtures of triglycerides that are extracted from plants, typically from plant seeds. Vegetable oils typically have a relatively high content of unsaturated fatty acids (typically up to 80%), including monounsaturated fatty acids (MUFA) and polyunsaturated fatty acids (PUFA), as well as some saturated fatty acids. The high content of unsaturated fatty acids makes most vegetable oils liquid at room temperature and suitable for various uses such as frying food. Animal fats as well as coconut and palm oils are solid or semi-solid at room temperatures (typically with melting temperatures between 22° C.-25° C.) due to their relatively high content of saturated fatty acids (typically around 50% in animal fats and around 80%-90% in coconut and palm oils). However, even coconut and palm oils which have a high content of saturated fatty acids (about 90% and 50% respectively), still include unsaturated fatty acids—about 9% in coconut oil and 50% (40% oleic acid and 10% polyunsaturated fatty acids) in palm oil. Frying oil that is made of vegetable oils may comprise antioxidants (e.g., ascorbic and/or acetic acids) that are added to counter the oxidation of the unsaturated fatty acids and increase the shelf life.

MCT (medium-chain triglycerides) oil 60/40 is produced by re-esterifying glycerol with caprylic acid (C8) and capric acid (C10) at a 2:1 ratio of fatty acids in the triglyceride, yielding an approximate 60:40 mass ratio between the fatty acids (typically within a range of between 55:45 and 65:35)—to yield liquid synthetic oil that is made of saturated fatty acids. The shorter carbon chains keep the MCT oil liquid at room temperatures in contrast to longer carbon chains of saturated fatty acids in solid and semi-solid fats. Fully saturated fats have the advantage of being highly resistant to peroxidation, the process in which hydrogen is removed from the double bond in the chain and a peroxide free radical is produced. Peroxidation of unsaturated fatty acids is the primary oxidation process of edible, mainly vegetable, fats and oils.

Natural oils and fats which contain mixtures of triglycerides with different molecular weights tend to separate under external influences such as gravity or centrifugation forces, changes in temperature beyond the solidification or melting points of at least one of the component triglycerides and thermal cycling between freezing and thawing. Natural mixed fats such as butter, coconut oil, olive oil etc. thus separate or fractionate naturally under such conditions with lighter fractions floating and heavier fractions sinking. For example, during preparation of chocolate, phase separation of oils and fats in the mixture is a common pitfall in the tempering process. Separation of oils and/or fats reduces the homogeneity of the fat and renders it less useful. For this reason, simple mixing of different fats in order to achieve a desired viscosity or melting temperature has limited usability.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides taste-enhanced liquid, semi-solid and/or solid oil-based suspensions consisting of a carrier oil and edible solid particles having median diameter of less than 15 μm, wherein the edible solids comprise crystalline salt and/or sugar, and optionally spices.

One aspect of the present invention provides a method of preparing an oil-based suspension, wherein the method comprising: mixing edible solid particles with a carrier oil to yield an oil-particles mixture, wherein the edible solids comprise crystalline salt and/or sugar, and optionally spices, and reducing a particle size of the edible solid particles in the oil-particles mixture to yield a liquid oil-based suspension with edible solid particles having a median particle size of between 0.1 and 15 μm.

One aspect of the present invention provides a method of preparing a fully saturated solid or semi-solid oil-derivative for a food product, the method comprising: defining a required temperature-viscosity profile and/or a required melting temperature of the solid or semi-solid oil derivative, deriving a required profile of triglycerides with saturated fatty acids for the oil-derivative to yield the required viscosity profile and/or a required melting profile, and following separation, heat distillation and fractionation of raw vegetable oil—re-esterifying the saturated fatty acids from the distilled components and optionally from an external source according to the required profile, to yield the solid or semi-solid oil derivative having a melting temperature above 15° C.

One aspect of the present invention provides a fully saturated solid or semi-solid oil-derivative for a food product, the solid or semi-solid oil-derivative comprising triglycerides of a plurality of saturated fatty acids, wherein the saturated fatty acids comprise at least one saturated fatty acid having 12 carbons or more, selected to provide a required temperature-viscosity profile and/or a required melting temperature profile of the oil-derivative that corresponds to the food product.

One aspect of the present invention provides a frying oil comprising triglycerides that include mostly, e.g., at least 98% saturated fatty acids and optionally comprises antioxidants.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1 is a high-level schematic illustration of an oil-based suspension and its preparation method, according to some embodiments of the invention.

FIG. 2 is a schematic illustration of prior art sweet or salty emulsion-based products.

FIGS. 5A-5D provide images of concentrated sweetened paste produced from the oil-based suspension, according to some embodiments of the invention.

FIG. 6A is a high-level schematic illustration of prior art production of MCT oil.

FIG. 8 is a high-level flowchart illustrating development and/or or production methods, according to some embodiments of the invention.

Figure 3:
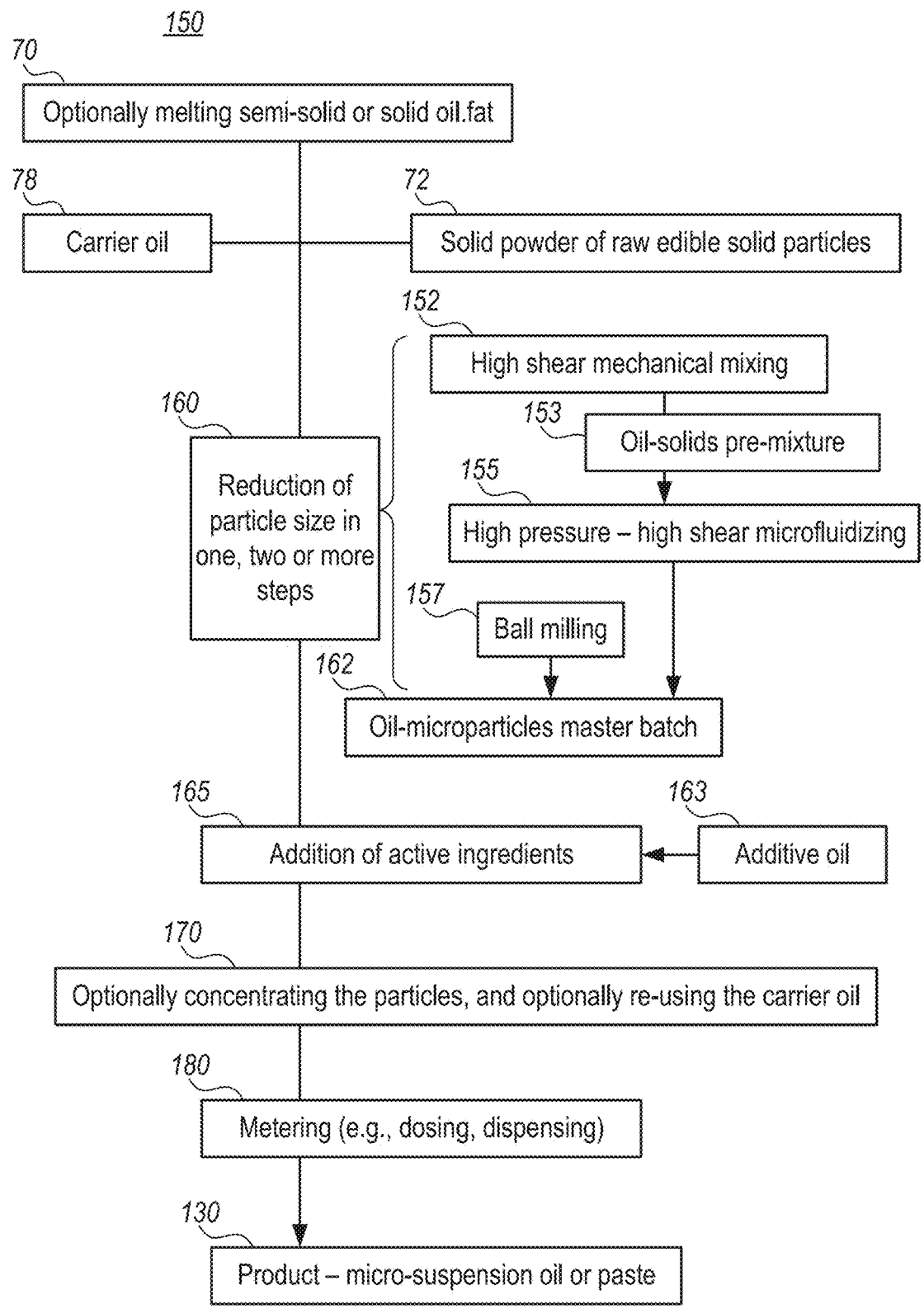
FIG. 3 is a high-level schematic illustration of preparation method(s) of oil-based suspension, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Embodiments of the present invention provide efficient and economical methods and mechanisms for producing taste-enhanced oil-based compositions and thereby provide improvements to the technological field of food industrial applications. Taste-enhanced liquid, semi-solid and/or solid oil-based suspensions are provided, which consist of a carrier oil and edible solid particles (e.g., crystalline salt and/or sugar, and optionally spices) having median diameter of less than 15 μm. The particles are reduced in size in the suspension, allowing enhancement of their organoleptic effects while reducing their amount to meet nutritional demands.

Embodiments of the present invention provide efficient and economical methods and mechanisms for producing solid or semi-solid oil derivatives that are resistant to oxidation for food products and thereby provide improvements to the technological field of food engineering and nutrition. Methods of preparing solid or semi-solid oil-derivative(s) for specific food products and applications as well as the respective solid or semi-solid oil derivatives are provided. The solid or semi-solid oil-derivatives comprise triglycerides of saturated fatty acids, including at least one saturated fatty acid having 12 carbons or more—selected to provide a required temperature-viscosity profile and/or a required melting temperature profile of the oil-derivative that corresponds to the food product. The methods derive the required profile of saturated fatty acids in the solid or semi-solid oil-derivative to yield the required temperature-viscosity profile and/or a required melting temperature profile of the food application, and addition of specific saturated fatty acids and optionally edible solids yield the predefined required properties of the food product.

Embodiments of the present invention provide efficient and economical methods and mechanisms for producing non-oxidizing frying oil and thereby provide improvements to the technological field of food preparation. Non-oxidizing frying oil is provided, based on saturated fatty acids. The frying oil comprises triglycerides that include mostly, e.g., at least 90%, at least 95%, at least 98%, at least 99% or 100% saturated fatty acids, as well as small amounts of antioxidants that prevent residual oxidation of the oil during prolonged frying.

FIG. 1 is a high-level schematic illustration of an oil-based suspension 130 and its preparation method 150, according to some embodiments of the invention. Oil-based suspension 130 may comprise taste-enhanced liquid oil-based suspension 130 consisting of a carrier oil 78 and edible solid particles 120 having a median diameter of less than 15 μm. Edible solid particles 120 may be made of raw edible solid particles 72 which are reduced in size by one or two orders of magnitudes (e.g., from hundreds of microns to tens, few, or event under one micron) and may comprise crystalline salt and/or sugar, spices, and/or other ingredients such as herbal or other medicines, minerals, amino acids and/or vitamins in solid powder phase. A mixture 122 of carrier oil 78 with raw edible solid particles 72 may be followed by one or more processing stages of particle size reduction, yielding suspension 130 with micronized particles. As a result, edible solid particles 120 in suspension 130 may have a final median diameter of less than any of 50 μm, 15 μm, 5 μm, or 1 μm, or intermediate values.

FIG. 1 further provides examples (optical microscope photographs) of sugar particles after a first reduction step (using, e.g., a food processor) to a particle size of less than 150 μm, and after a second reduction step (using. e.g., a microfluidizer) to a particle size of less than 40 μm.

Suspension 130 may have an edible solid content of between 1% and 30% w/w (or even higher following concentration—see below). In various embodiments, suspension 130 may have an edible solid content of any of 1%, 3%, 5%, 10%, 15%, 20%, 25%, 30% w/w edible solid particles, or intermediate values. Suspension 130 may include between 50% and 99% w/w carrier oil. In various embodiments, suspension 130 may include a carrier oil content of any of 99%, 95%, 90%, 80%, 70%, 50%, w/w carrier oil, or intermediate values. Additional oil, e.g., with specific active ingredients may be added to suspension 130 of carrier oil 78 and edible particles 120, as disclosed below.

Carrier oil 78 may comprise any of medium chain triglyceride (MCT) oil, other synthetic oils (e.g., as disclosed below), canola oil, coconut oil, peanut butter oil, palm oil, olive oil, fish oil, sunflower seed oil, soy oil, or any combination thereof. In certain embodiments, carrier oil 78 may comprise warmed or heated solid or semi-solids such as any of melted butter, melted cocoa butter, melted peanut butter, etc. Carrier oil 78 may comprise saturated oil(s) and/or unsaturated oil(s) and may be at least partly resistant to oxidation and/or include antioxidant(s) (e.g., as disclosed below). Carrier oil 78 may be any of inert, tasteless and/or odorless.

Edible solid particles 120 may comprise any of sugar (of any type, e.g., any of sucrose, fructose, glucose, galactose, lactose, maltose, xylose, glycerol, sorbitol, corn syrup solids, maltodextrin, aspartame, sucralose, acesulfame, xylitol), salt (of any type, e.g., sea salt), various spices (e.g., pepper, paprika, cardamom, nutmeg, oregano, turmeric, cumin, sage and the like), any kind of herbal medicine, medicine, minerals, lipophilic amino acids, vitamins (e.g., vitamin C powder) and/or combinations of any of the above. Edible solid particles 120 may be selected and configured to provide any desired organoleptic sensation. e.g., taste, smell or other feeling, possibly enhanced by the reduced particle size of edible solid particles 120.

Non-limiting examples for products that can be made of suspension 130 include stable sweetened fish oil, chocolate products (e.g., after mixture of suspension 130 with cocoa products such as cocoa butter), sweetened or salted peanut butter (e.g., after mixture of suspension 130 with peanut butter), sweetened, salted or spiced dairy butter (e.g., after mixture of suspension 130 with dairy butter), sweetened, salted or spiced edible oil (e.g., after mixture of suspension 130 with olive oil, coconut oil, any other vegetable oils or any other edible oil), sweetened, orally administered, medicinal product (e.g., after mixture of suspension 130 with any kind of medicine, vitamins, lipophilic amino acids or minerals that may be water immiscible), or other products (e.g., after mixture of suspension 130 with dairy butter, cream, coconut oil, palm oil, animal fat or any other edible fat and oil based products).

For example, consumable products may comprise sweetened fish oil including 75-95% w/w of carrier oil 78 which may comprise fully or partly of fish oil and between 1-25% w/w of edible solid particles in suspension 130. In a non-limiting example, a product may include 76.7 wt. % fish oil, 3.5 wt. % sugar suspended in 19.8 wt. % carrier oil (e.g., MCT).

Consumable product comprising liquid oil-based suspension 130 may include between 1% and 100% w/w of suspension 130. In various embodiments, suspension 130 may have an edible solid content of any of 1%, 3%, 5%, 10%, 15%, 20%, 25%, 30%, 40%, 50%, 60%, 70%, 80%, 90%, 95%, 99%, 100% w/w of suspension 130, or intermediate values, and may include any food industry or pharmaceutical industry products.

FIG. 2 is a schematic illustration of prior art sweet or salty emulsion-based products. Typically, prior art emulsion-based products have high content of sugars and/or salt and require use of additives such as water, emulsifiers and stabilizers. In the illustrated example, sugar crystals added to current products are typically large, from 2 mm down to about 0.5 mm (illustrated is a 545 μm sugar crystal).

Advantageously, disclosed oils with microparticles of edible solids solve the need for oil-based formulations comprising, sugars, salts, spices and other water-soluble ingredients, without requiring the use of additional ingredients such as water or stabilizers (e.g., starch), and providing desired organoleptic sensations of enhanced flavoring, even at a reduced content of the edible solids (e.g., sugar or salt). For example, disclosed sweetened oils may be used in products having a high oil content such chocolate, sweetened peanut butter, etc. Disclosed methods enable mixing hydrophilic materials such as sugar, salt or other polar molecules in oil, fats or in products having a high oil content, without addition of water, emulsifiers or stabilizers. Moreover, the use of micro particles overcomes prior art issues with using potentially explosive sugar dust having the particles are under 500 μm, without using additives such as starch.

Advantageously, disclosed oils may include water-sensitive components, water-based emulsions are not required to dissolve sugar, salt or other hydrophilic components of the product. For example, disclosed oils may include Ω3 fatty acids, olive oil, plant oils, Ω6 fatty acids etc. which are sensitive to oxidation. Moreover, food safety is enhanced by enabling the use of dry components such as spices which are better protected against microbial activity and preserve their organoleptic properties in dry (water free) environment—increasing the products' shelf life and quality.

Advantageously, disclosed embodiments reduce the amount of required sugar and/or salt, resulting in a much lower caloric content and/or sodium content than current products. For example, while current product may reach a 50% w/w of sugar to reach a given level of sweetness, disclosed products may require a much smaller amount due to the micron dimensions of used sugar crystals. Also, disclosed embodiments may reduce the use of sweeteners to replace sugar, as disclosed embodiments require a much smaller amount of sugar.

FIG. 3 is a high-level schematic illustration of preparation method 150 of oil-based suspension 130, according to some embodiments of the invention. Mixing carrier oil 78 and/or optionally melted semi-solid or solid fat/oil 70 (e.g., butter, cocoa butter, peanut butter, etc.) with raw edible solid particles 72 may be followed by one or more processing stages 160 that reduce the size of raw particles 78 to reach micronized particles 120. For example, high shear mechanical mixing 152 may be used to yield an oil-solids pre-mixture 153, followed by high pressure-high shear microfluidizing 155 that yields oil-microparticles master batch 162, which may provide final suspension 130 or be further processed, e.g., by addition of active ingredients 165 such as additive oil(s) 163. e.g., including one or more active ingredients. Mixing oil-based suspension 130 with additive oil(s) 163 may be carried out under conditions that maintain the homogeneity and stability of suspension 130 and prevent its oxidation, e.g., over several or tens of minutes and under inert conditions (e.g., $N_2$ or Ar atmosphere).

In various embodiments, carrier oil 78 may comprise synthetic oils such as MCT or synthetic saturated oils as disclosed below to use the high degree of fluidity of these oil (e.g., MCT is almost as liquid as water under room temperatures). The fluidity of carrier oil 78 is used to generate suspension 130 and the following particle size reduction efficiently.

In certain embodiments, micronized particles 120 may be concentrated in suspension 130 to higher densities to increase their concentration (stage 170), e.g., above 30% w/w, or between 15% to 75% w/w. The concentration of micronized particles 120 may be selected to determine the consistence of suspension 130. e.g., from highly liquid (e.g., 15% w/w or lower), through semi-solid (e.g., 30%-50% w/w, depending on the type and size of micronized particles 120 and on carrier oil 78) to solid butter-like material (e.g., 50%-75% w/w depending on the type and size of micronized particles 120 and on carrier oil 78). For example, concentration 170 using centrifugation is provided as a non-limiting example below. In various embodiments, suspension 130 may have an edible solid content of any of 15%, 20%, 25%, 30%, 35%, 40%, 45%, 50%, 55%, 60%, 65%, 70%, 75% w/w edible solid particles, or intermediate values. The more solid suspension 130 is made, the easier it may be handled and transported. In certain embodiments, carrier oil 78 may be extracted upon concentration of suspension 130 and optionally be re-used for preparing additional suspension 130.

Following the preparation of suspension 130 it may be metered (step 180. e.g., dosed or dispensed in a controlled amount) and the product micro-suspension oil 130 may be provided, and possible further processed to yield semi-solid and/or solid products as disclosed below. Resulting micro-suspension oil 130 may consist of edible solid crystalline particles having a median particle size of between 0.1 and 15 μm. Micro-suspension oil 130 may be stable for 5-60 minutes (e.g., when used to prepare a semi-solid or solid product) or micro-suspension oil 130 may be stable for several hours, days, weeks or months, especially with small particle size (e.g., tenths of microns or even less that 100 nm), and without addition of any stabilizer. In certain embodiments, suspension 130 may be configured to enable reinstitution of the homogeneous microparticle distribution following possible sedimentation, e.g., by agitating suspension 130.

The reduction of the particle size (step 160) may be performed in 1, 2, 3, 4 or 5 steps, wherein the particle size is reduced in each consecutive step. Raw edible solid particles 72 may have a particle size of 500 μm, 250 μm, intermediate or lower values, and be reduced to a median particle size of particles 120 e.g., between 0.1-15 μm, 1-50 μm or within intermediate ranges. For example, high shear mechanical mixing 152 may comprise using a food processor to reduce the median particle size of the edible solid particles from between 250-500 μm to between 50-150 μm and high pressure-high shear microfluidizing 155 may comprise using a microfluidizer to reduce the median particle size of the edible solid particles from between 50-150 μm to between 0.1-15 μm, between 1-50 μm, between 0.1-100 μm, or within intermediate ranges.

For example, using a food processor may be carried out for one or more periods between 1 and 5 minutes, with intervals of few or tens of seconds (e.g., between 1-60, e.g., 30, 40, 50, 60, 70 or 80 seconds) between consecutive operation periods (e.g., up to 6 consecutive operation periods).

In certain embodiments, particles size reduction may be carried out in a single stage, e.g., by a microfluidizer from a particle size between 250-500 μm to between 0.1-100 μm, 1-50 μm, between 0.1-15 μm or within intermediate ranges. Non-limiting examples for operation parameters of the microfluidizer include a pressure of between 5,000 and 40,000 psi (e.g., between 20.000-23,000 psi) and channels sizes between 75 μm to 1100 μm (e.g., any of 75 μm, 87 μm, 100 μm, 125 μm, 150 μm, 200 μm, 250 μm, 300 μm, 400 μm, 425 μm, 550 μm, 1100 μm, or intermediate values). One or more microfluidizers with different channel sizes may be used. e.g., a first microfluidizer with channel size of hundreds of microns (e.g., between 200-550 m) and a second microfluidizer with channel size of tens of microns (e.g., between 75-125 μm). High pressure-high shear microfluidizing 155 may be applied. e.g., 1 to 10 consecutive time (e.g., intermediate values, or 4-7 times, or 5-6 times) to gradually reduce the particle sizes.

Figure 4A:
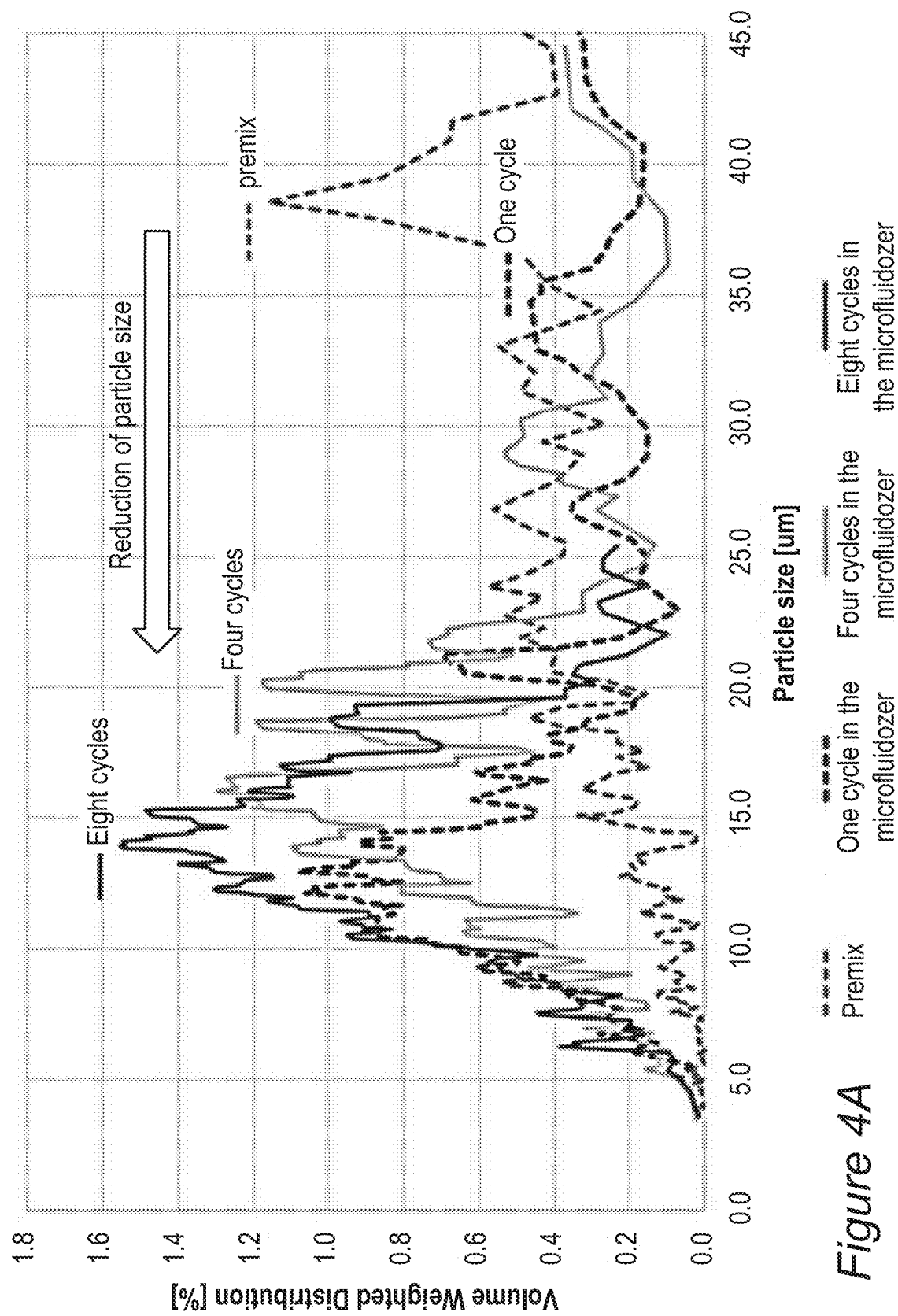
FIGS. 4A and 4B provide experimental data concerning the particles size distribution in suspension, according to some embodiments of the invention.
Figure 4B:
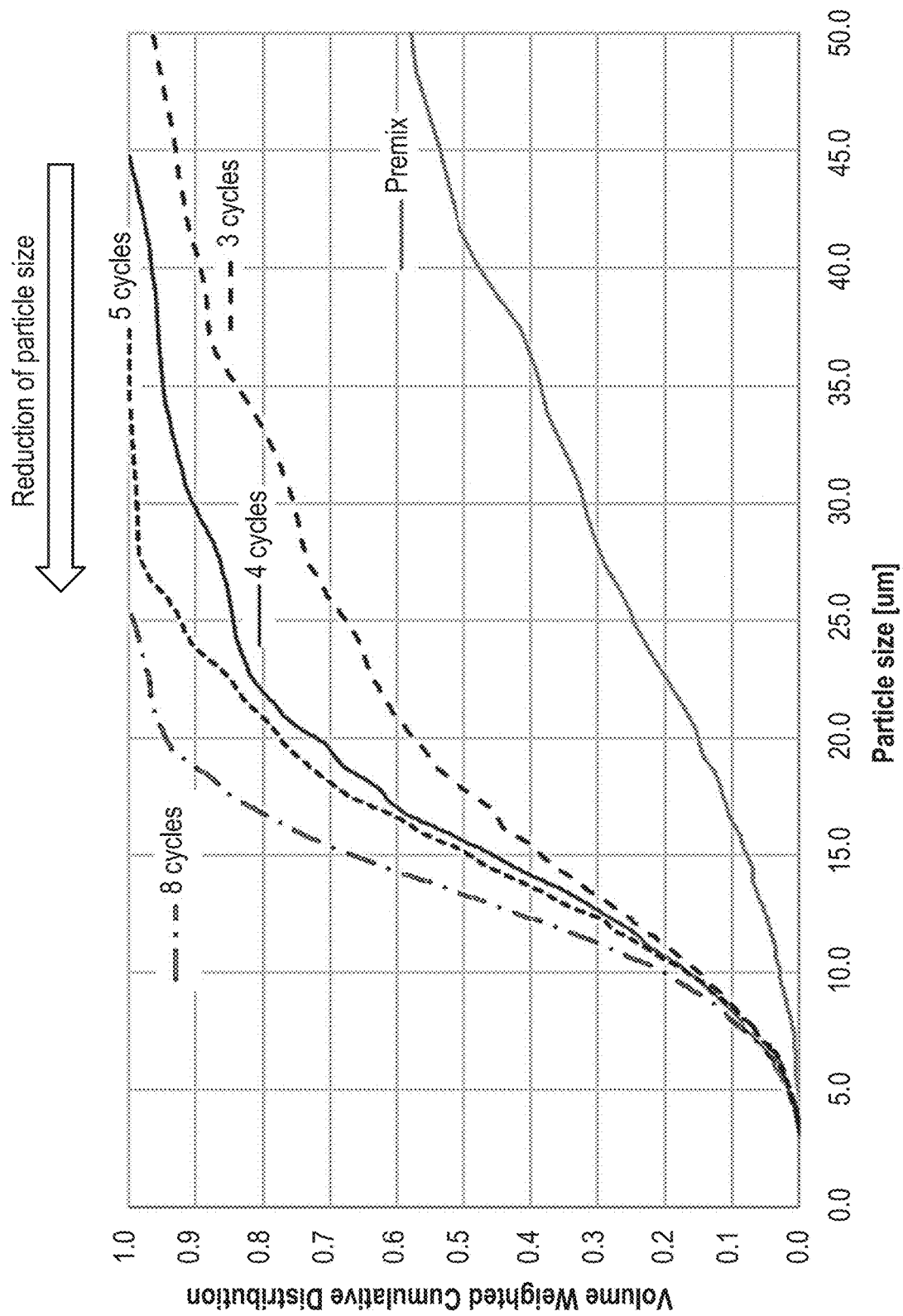

For example, FIGS. 4A and 4B provide experimental data for sugar, concerning the particles size distribution in suspension 130, according to some embodiments of the invention. FIG. 4A illustrates reduction 160 in particle size over consecutive cycles of microfluidizing 155, providing the volume-weighted distribution of particle size in pre-mixture 153 and after one, four and eight microfluidizing 155 cycles using a microfluidizer with a channel of 87 μm. FIG. 4B illustrates reduction 160 in particle size over consecutive cycles of microfluidizing 155, providing the cumulative volume-weighted distribution of particle size in pre-mixture 153 and after one, three, four, five and eight microfluidizing 155 cycles using the same microfluidizer.

FIGS. 4A and 4B indicate that premix 153 has a wide particle distribution with relatively large particles (between 10-100 μm diameter, median particle size of 42 μm). The reduction steps were conducted in the microfluidizer, using a channel of 87 μm. A reduction in particle size distribution was observed even after a single cycle. The particle sizes decreased upon consecutive microfluidizing stages 155, reaching a particle size distribution between ca. 5-50 μm diameter, median particle size of 16 μm after four cycles, and a particle size distribution between ca. 5-20 μm diameter, median particle size of 13 μm after eight cycles.

In certain embodiments, particle size reduction 160 may be carried out at least partly by ball milling 157 (instead or in addition to pre-mixing 152 and/or microfluidizing 155). Advantageously, ball milling 160 may be used to process viscous carrier oils 78, and possibly to fluidize semi-soli or solid oils/fats to be used as carriers 78 for the particles and support their micronization process. For example, the following results have been achieved using WAB@ Dyno®-Mill MultiLab 1.4

As an example for concentration and solidification of suspension 130 by centrifugation, 163 gr of suspension 130, made of MCT oil with 15% (25 gr) of suspended sugar microparticles 120 were centrifuged for 5 minutes at 5000 rpm (acceleration of 2800 g) to yield 33 gr of paste 130 and 130 gr of carrier oil for re-use. Paste 130 thus reached a 75% w/w sugar microparticles concentration, and had a consistency of a soft solid, or a butter-like semi-solid at room temperature, as shown in FIGS. 5A and 5B. Centrifugation at lower intensity (3 minutes at 1000 rpm, acceleration of 111 g) yielded 111 gr of viscous suspension 130 with sugar concentration of 15% w/w—illustrating the ability to control sugar concentration and consistency of suspension 130 by modifying centrifugation parameters (such as duration and rotation speeds).

In various additional runs, a range of concentrations of suspension 130 were checked, ranging in sugar concentration between 15% w/w to 65% w/w, and in consistency from fluid (FIG. 5C) to solid (FIG. 5D), respectively—further indicating the control of sugar microparticles concentration and consistency of suspension 130 by centrifugation 170, according to some embodiments of the invention. Advantageously, different types of suspension 130 may be used in different industrial segments for different uses as disclosed herein.

Various embodiments comprise consumable products comprising liquid oil-based suspensions 130 and/or taste-enhanced pastes separated from centrifugated liquid oil-based suspension 130. Various embodiments comprise fully saturated solid or semi-solid oil-derivative disclosed below, which comprises triglycerides of saturated fatty acids with at least one saturated fatty acid thereof having 12 carbons or more. For example, carrier oil 78 may comprise melted fully saturated solid or semi-solid oil-derivative(s) (denoted 105) as disclosed below.

FIG. 6A is a high-level schematic illustration of prior art production of MCT oil. In prior art 90, MCT (medium-chain triglycerides) are distilled from coconut and palm kernel oil 80, and MCT is produced by re-esterifying the glycerol with caprylic acid (C8) and capric acid (C10) to yield MCT oil 60/40, which is a synthetic MCT oil 95 made of triglycerides having a mass ratio of about 60:40 between caprylic acid (C8) and capric acid (C10) (corresponding to a 2:1 ratio of the fatty acids in the triglyceride) and a melting point at about 5° C.

The production process includes physical vacuum distillation with separation, heat distillation and fractionation of raw vegetable oil 80 (stage 225) to yield glycerol and medium-chain fatty acids (MCFAs) separated by molecular weight (chain lengths: C6-caproic acid, C8-caprylic acid, C10-capric acid, C12-lauric acid; for example, in weight fractions of 2%, 38%, 58%, 2%, respectively), as illustrated schematically. Other commercially available options of MCT include for example 100% caprylic acid (C8); 100% capric acid (C10); 80% caprylic acid (C8) and 20% capric acid (C10); and other combinations of caprylic acid (C8), capric acid (C10).

Figure 6B:
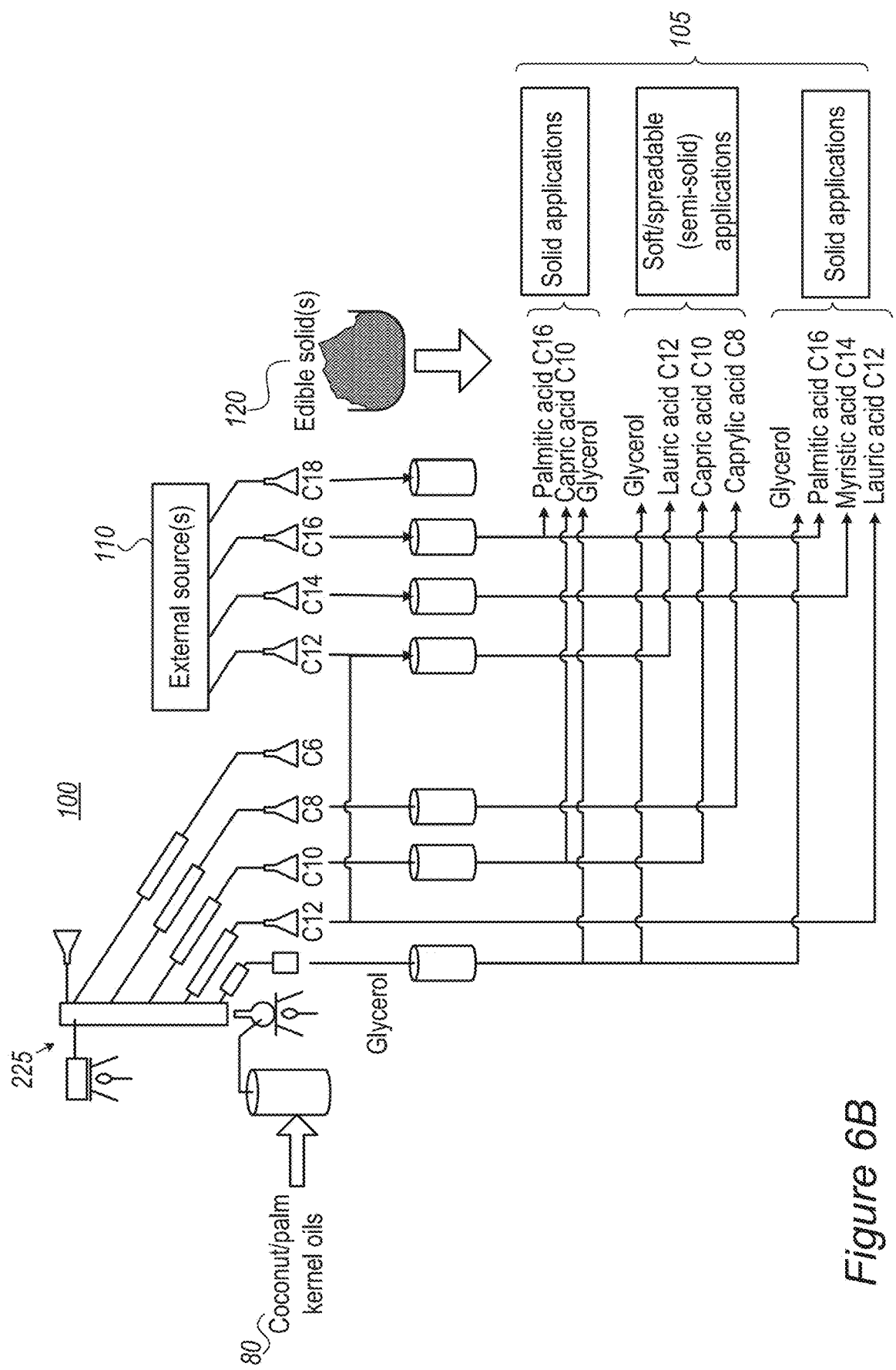
FIGS. 6B and 7 are high-level schematic illustrations of production methods and development processes for preparing an oil-derivative for a food product, according to some embodiments of the invention.
Figure 7:
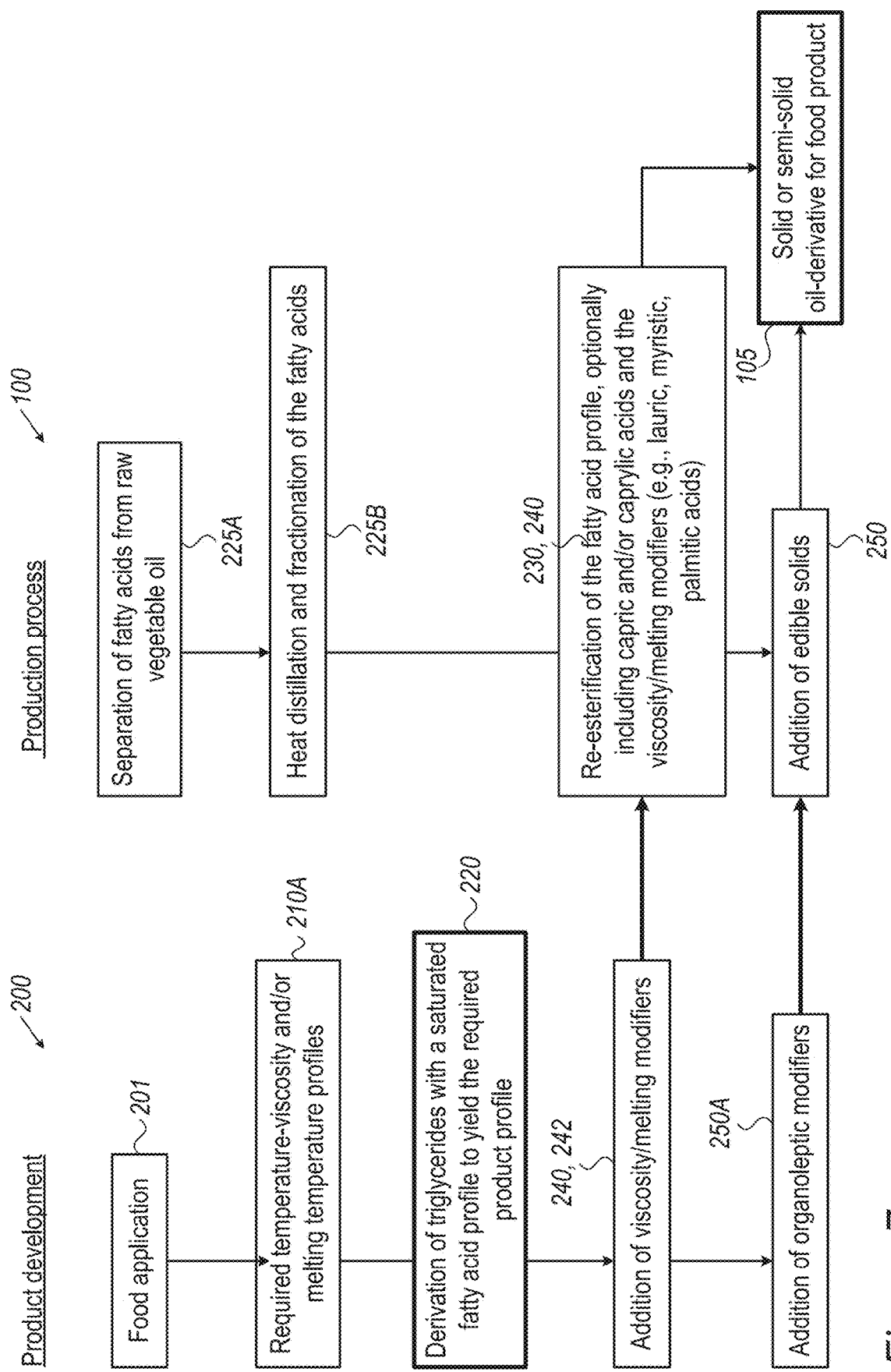

FIGS. 6B and 7 are high-level schematic illustrations of production methods 100 and development processes 200 for preparing an oil-derivative 105 for a food product 201, according to some embodiments of the invention. FIG. 6B is a non-limiting schematic illustration of disclosed production processes 100, while FIG. 7 is a high-level block diagram of product development 200 and associated production process 100, according to some embodiments of the invention. FIG. 8 is a high-level flowchart illustrating development and/or or production method 200, according to some embodiments of the invention. The method stages may be carried out with respect to production process 100 described herein, which may optionally be configured to implement method 200. Elements from FIGS. 6B-8 may be combined in any operable combination, and the illustration of certain elements in certain figures and not in others merely serves an explanatory purpose and is non-limiting.

In disclosed embodiments (see, e.g., schematic FIG. 7), a production process 100 is provided to yield an oil-derivative 105 for a food product, made according to specifications for a food application 201 in a product development process disclosed herein as method 200. Disclosed oil-derivative 105 comprises triglycerides of a plurality saturated fatty acids, having at least one saturated fatty acid with 12 carbons or more that is selected to provide a required temperature-viscosity profile and/or a required melting temperature of oil-derivative 105, which corresponds to the food product and the requirements of food application 201. Additional fatty acids of the triglycerides may comprise shorter saturated fatty acids (e.g., caprylic acid and/or capric acid) and/or longer saturated fatty acids—according to the required temperature-viscosity and melting temperature profiles for the product.

For example, in production process 100 (see. e.g., FIG. 6B), the at least one saturated fatty acid with 12 carbons or more may comprise any of lauric acid (C12), myristic acid (C14), palmitic acid (C16) and/or stearic acid (C18)—which may be added from external source(s) 110, optionally including palm or coconut fat or other sources such as cocoa butter or synthetic sources. For example, lauric acid may be added as a distilled components of coconut and/or palm kernel oil 80 and/or from external source(s) 110 while longer chain saturated fatty acids may be added after separation from various fats.

Oil-derivative 105 may further comprise at least one edible solid 120 as organoleptic modifier. e.g., taste modifier, smell modifier or modifier of the look and feel of the food product. Oil-derivative 105 may be configured to have physical characteristics that are required by food application 201, for example, oil-derivative 105 may be configured to yield the food product (i) as a semi-solid spread (e.g., bread spread such as butter replacement or chocolate spread, e.g., including lauric acid to yield a melting temperature of 15° C.), (ii) as a solid (e.g., chocolate bar. e.g., including palmitic acid to yield a melting temperature of 35° C.), (iii) as a semi-solid soft food product (e.g., soft cake, e.g., including lauric acid to yield a melting temperature of 15° C.).

It is noted that the melting points of oil-derivatives 105 relate to the melting points of the triglycerides and their constituent fatty acids, as well as to their combinations and their positions on the glycerol backbone. The melting points of the free fatty acids indicate the transition points in which the solid phase fatty acid turns into the liquid phase, and are usually well-defined. For example, caproic acid (C6) has a melting temperature of −3° C. caprylic acid (C8) has a melting temperature of 17° C., capric acid (C10) has a melting temperature of 32° C. lauric acid (C12) has a melting temperature of 44° C., myristic acid (C14) has a melting temperature of 54° C., palmitic acid (C16) has a melting temperature of 63° C., stearic acid (C18) has a melting temperature of 70° C., arachidic acid (C20) has a melting temperature of 75° C., etc. It is noted that fatty acids with an odd number of carbon atoms typically have intermediate melting points.

Triglycerides typically have melting points that deviate from the melting points of their constituents. For example, synthetic tricaprylin (glycerol with three caprylic acids) has a melting point of 10° C. (lower than 17° C. for caprylic acid), synthetic tricaprin (glycerol with three capric acids) has a melting point of 32° C. (similar to 32° C. for capric acid), and synthetic trilaurin (glycerol with three lauric acids) has a melting point of 46° C. (higher than 44° C. for lauric acid), and synthetic trimyristin (glycerol with three myristic acids) has a melting point of 56° C. (higher than 54° C. for myristic acid). MCT oil provides another example, having a melting temperature of 5° C., which is significantly lower than the melting temperatures of either caprylic acid (17° C.) or capric acid (32° C.).

In various embodiments, oil-derivatives 105 may comprise triglycerides having two shorter fatty acids such as caprylic acid (C8) and/or capric acid (C10) and one longer fatty acid such as myristic acid (C14), palmitic acid (C16) and/or stearic acid (C18). The two shorter fatty acids may be different from each other or identical, and the longer fatty acid may be set at any position of the triglyceride. The melting point of these triglycerides may be intermediate between the melting points of the shorter fatty acids and the melting points of the longer fatty acid, and may be adjusting according to given requirements by modifying the exact triglyceride composition.

Accordingly, the melting point of oil-derivative 105 may be adjusted to its food application use to yield solid and/or semi-solid oil-derivative 105 by selecting the specific saturated fatty acids and their positions on the glycerol to yield a specified melting temperature (in general—the longer the fatty acid chains the higher the melting point).

As illustrated schematically in FIG. 7, product development process as method 200 may start from physical and chemical parameters of food application 201 that are used to define required temperature-viscosity and/or melting temperatures 210A. From these, the profile of saturated fatty acids may be derived to yield the required product profile (stage 220). Production process 100 of solid or semi-solid oil derivative 105 may then be modified beyond separation of fatty acids from raw vegetable oil 225A and heat distillation and fractionation of the fatty acids 225B—to include re-esterification of triglycerides with the derived fatty acid profile to include the viscosity/melting modifiers, optionally in addition to capric and/or caprylic acids (stages 240, 242, e.g., any of lauric, myristic, palmitic, stearic acids) (stages 230, 240). In certain embodiments, the triglycerides may comprise at least one fatty acid with a carbon chain of 12 carbons or more. Additionally, with relation to food application 201, addition of organoleptic modifiers 250A may be required, and implemented by addition of edible solids (stage 250) as disclosed herein, to yield required solid or semi-solid oil derivative 105 for the food product as defined by food application 201. Overall, disclosed product development and production processes enable to tailor and optimize specific oil compositions to specific food application specifications.

FIG. 8 is a high-level flowchart illustrating development and/or or production method 200, according to some embodiments of the invention. Method 200 may comprise preparing an oil-derivative for a food product (stage 205) by the disclosed stages, irrespective of their order.

Method 200 may comprise defining a required viscosity profile and/or a required melting profile of the solid or semi-solid oil derivative (stage 210), deriving a required profile of saturated fatty acids in the oil-derivative to yield the required viscosity profile and/or a required melting profile (stage 220), and, following separation, heat distillation and fractionation of raw vegetable oil (stage 225), re-esterifying triglycerides with the required profile of saturated fatty acids from the distilled components and optionally from an external source, to yield the solid or semi-solid oil derivative (stage 230), including in the solid or semi-solid oil derivative comprises at least one saturated fatty acid with 12 carbons or more, optionally in addition to caprylic and capric acids (stage 240).

Method 200 may further comprise selecting the at least one saturated fatty acid as modifier of a viscosity and/or melting temperature of the food product (stage 242). For example, method 200 may comprise using lauric acid from the distilled components as the at least one saturated fatty acid in addition to caprylic and capric acids (stage 244) and/or using myristic, palmitic and/or stearic acids from the external source as the at least one saturated fatty acid in addition to caprylic and capric acids (stage 246), and optionally adding at least one edible solid as organoleptic modifier to the solid or semi-solid oil derivative (stage 250).

Examples for edible solids 120 include sugars (e.g., any of sucrose, fructose, glucose, galactose, lactose, maltose, xylose, glycerol, sorbitol, corn syrup solids, maltodextrin, aspartame, sucralose, acesulfame, xylitol or any combination thereof), salts, spices (e.g., pepper, paprika, cardamom, nutmeg, oregano, turmeric, cumin, sage or any combination thereof) or combinations thereof. Edible solid(s) 120 may be added to solid or semi-solid oil derivative 105 at an amount between about 1% to 30% w/w and at particle sizes between 0.1 μm and 100 μm. Various compositions and characteristics of solid or semi-solid oil derivative 105 with suspended edible solids 120 may include any of the oil-based suspensions which are disclosed herein.

It is noted that a value modified by the term "about" is understood to encompass ±10% of the value.

Advantageously, solid or semi-solid oil derivative 105 may comprise only saturated fatty acids and be used in a wide range of products—due to its solid or semi-solid consistence. It is noted that alleged heath detrimental effects of saturated fatty acids typically refer to fats combining saturated and unsaturated fatty acids (e.g., animal fats), and there exists substantial controversy concerning these detrimental effects. In fact, food products that include only saturated fatty acids may have health and commercial advantages as well as longer shelf life—as the saturated fatty acids are much less susceptible to oxidation than unsaturated fatty acids.

In various embodiments, taste-enhanced liquid oil-based suspension 130 and/or solid or semi-solid oil derivative 105 may comprise any of the following heterogenous triglycerides (esters derived from glycerol and three non-identical fatty acids) that have only saturated fatty acids. Such heterogenous triglycerides may have health and commercial advantages when consumed directly and/or when used to prepare and/or fry food—as the saturated fatty acids are much less susceptible to oxidation than unsaturated fatty acids. As a result, disclosed triglycerides have a longer shelf life and may also have health benefits. It is noted that alleged health detrimental effects of saturated fatty acids typically refer to fats combining saturated and unsaturated fatty acids (e.g., animal fats), and there exists substantial controversy concerning these detrimental effects. Disclosed triglycerides with only saturated fatty acids may have solid or semi-solid consistence and be used in a wide range of products. For example, carrier oil 78 may comprise or consist of MCT oil and/or one or more of the disclosed heterogenous triglycerides.

Disclosed heterogenous triglycerides may be prepared to have any profile of viscosity versus temperature and any desired melting temperature as disclosed herein, while resisting separation due to external influences, thereby overcoming the limitation of simple mixing of fats and oils for this purpose.

For example, triglycerides are disclosed, which include caprylic acid, capric acid and palmitic acid as fatty acids. While caprylic acid and capric acid are the fatty acids in synthetic MCT oil, no synthetic oils or fats include palmitic acid as one of the fatty acids.

In various embodiments, disclosed triglycerides may comprise three aliphatic saturated fatty acids that include at least one fatty acid with more than ten carbon atoms. For example, disclosed triglycerides may comprise caprylic acid, capric acid and palmitic acid—yielding glyceryl-caprylate-palmitate-caprate as illustrated below.

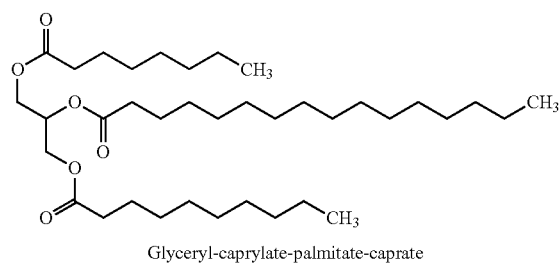 [SMILES: CCCCCCCCCCCCCCCC(=O)OC(COC(=O)CCCCCCC)COC(=O)CCCCCCCCC]

Glyceryl-caprylate-palmitate-caprate

It is noted that the palmitic acid may be at the central position (sn-2) of the glycerol, or may be at one of the side positions (sn-1, sn-3). Certain embodiments comprise triglycerides with two palmitic acids, at any two positions (e.g., sn-2&1, sn-2&3, sn-1&3), with a different saturated fatty acid at the remaining position (e.g., caprylic acid or capric acid, or longer chain saturated fatty acids, e.g., lauric acid, myristic acid, etc.).

In some embodiments, disclosed triglycerides may comprise caprylic acid, capric acid and any one of lauric, myristic or stearic acid, e.g., glyceryl-caprylate-myristate-caprate as illustrated below.

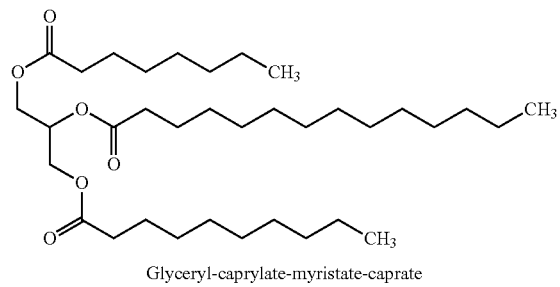 [SMILES: CCCCCCCCCCCCCC(=O)OC(COC(=O)CCCCCCC)COC(=O)CCCCCCCCC]

Glyceryl-caprylate-myristate-caprate

It is noted that the lauric, myristic or stearic acid may be at the central position (sn-2) of the glycerol, or may be at one of the side positions (sn-1, sn-3). Certain embodiments comprise triglycerides with two lauric, myristic or stearic acids, at any two positions (e.g., sn-2&1, sn-2&3, sn-1&3), with a different saturated fatty acid at the remaining position (e.g., caprylic acid or capric acid, or longer chain saturated fatty acids, e.g., lauric acid, myristic acid, etc.). Specifically, disclosed triglycerides may comprise three saturated fatty acids that have 12 or more carbons, with at least one of the fatty acids different from the others.

In some embodiments, disclosed triglycerides may comprise at least two fatty acids with more than ten carbon atoms, e.g., any of lauric acid, myristic acid, palmitic acid and/or stearic acid. The third fatty acid may comprise caprylic acid or capric acid, e.g., glyceryl-myristate-caprylate-stearate and glyceryl-myristate-caprylate-palmitate as illustrated below.

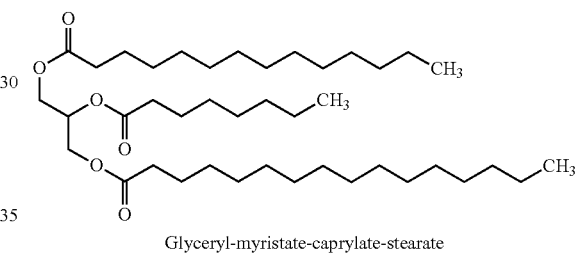

Glyceryl-myristate-caprylate-stearate

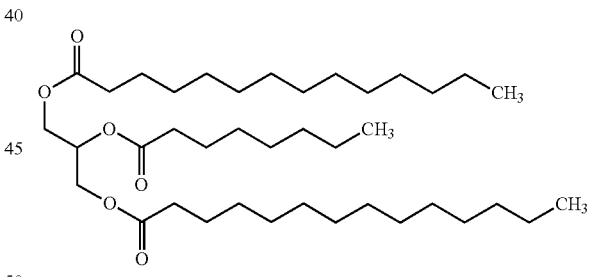

Glyceryl-myristate-caprylate-palmitate

Another example includes glyceryl-caprylate-laurate-palmitate (C8:C12:C16) or any other heterogenous combination of at least one C12 to C18 saturated fatty acid and another two C8 to C18 saturated fatty acids. The saturated fatty acids in these heterogenous triglycerides may be set at any available position of the glycerol.

In certain embodiments, one, two or three saturated fatty acids with an odd number of carbons may be esterified with glycerol and a complementary number of saturated fatty acids with an even number of carbons to form disclosed triglycerides.

Table 1 provides examples for triglyceride compositions, according to some embodiments of the inventions.

TABLE 1

| | Disclosed triglyceride compositions | | |
|---|---|---|---|
| Composition of saturated fatty acids: | Heterogenous | One or more saturated fatty acid with more than 10 carbons | Even and/or odd number of carbons |
| Examples: | Two or three different types of saturated fatty acid in the triglyceride | Lauric, myristic, palmitic and/or stearic acids | |
| Consistence of the resulting fat: | Liquid (melting temperature below about 15° C.) | Semi-solid (melting temperature between about 15° C. and 32° C.) | Solid (melting temperature above about 32° C.) |

Certain embodiments comprise a heterogenous triglyceride comprising three aliphatic saturated fatty acids, represented by structure X, wherein x, y and z are each individually an integer between 6 and 22, at least one of x, y and z is an integer of at least 10; and x, y and z are not identical.

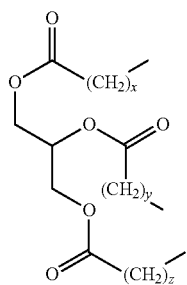

It is noted that an aliphatic saturated fatty in structure X with an integer of 6 corresponds to linked caprylic acid, an aliphatic saturated fatty acid in structure X with an integer of 8 corresponds to linked capric acid, an aliphatic saturated fatty acid according to structure X with an integer of 10 corresponds to linked lauric acid, an aliphatic saturated fatty acid according to structure X with an integer of 12 corresponds to linked myristic acid, an aliphatic saturated fatty acid according to structure X with an integer of 14 corresponds to linked palmitic acid, and an aliphatic saturated fatty acid according to structure X with an integer of 16 corresponds to linked stearic acid.

It is noted that in various embodiments, disclosed heterogenous triglyceride may include two shorter fatty acids such as caprylic acid (C8) and/or capric acid (C10) and one longer fatty acid such as myristic acid (C14), palmitic acid (C16) and/or stearic acid (C18). The two shorter fatty acids may be different from each other or identical, and the longer fatty acid may be set at any position of the triglyceride. The melting point of these triglycerides may be intermediate between the melting points of the shorter fatty acids and the melting points of the longer fatty acid, and may be adjusting according to given requirements by modifying the exact triglyceride composition.

Various embodiments comprise mixtures of disclosed heterogenous triglycerides, wherein two or more triglycerides have a common melting temperature within any of 1-3° C., 1-5° C. or 1-10° C. of each other. Various embodiments comprise solid or semi-solid fats comprising one, two or more of the disclosed heterogenous triglycerides, which may have a melting temperature lower than 50° C., or lower than 45° C., or lower than 40° C., or lower than 35° C. Various embodiments comprise liquid oils fats comprising one, two or more of the disclosed heterogenous triglycerides, which may have a melting temperature lower than 20° C. or lower than 15° C., or lower than 10° C. In embodiments. MCT oils may comprise between any of 1-30%, 1-50%, or 1-99% by weight of disclosed liquid oils. Various embodiments comprise composition(s) comprising one, two or more of the disclosed heterogenous triglycerides, which may include the triglycerides at a purity of >70%, at a purity of >80%, at a purity of >90%, at a purity of >95%, or at a purity of >99%. Various embodiments comprise foodstuffs with any of the disclosed heterogenous triglycerides, mixtures, solid or semi-solid fats, liquid oils and/or compositions thereof.

Certain embodiments include mixtures of disclosed triglycerides, having in common a melting temperature within a certain narrow range (e.g., 1-3° C., 1-5° C., or 1-10° C.), that prevents separation of the components under external influences such as gravity or centrifugation forces, changes in temperature and thermal cycling between freezing and thawing. For example, oils and fats that include one type of triglyceride with specified saturated fatty acids fully resist separation to phases that is typical for natural fats, as they include only one phase.

Certain embodiments comprise liquid oils comprising any of the disclosed triglycerides or any combination thereof. Liquid oils may comprise between 1-99% of disclosed heterogenous saturated triglycerides, with other components having different triglycerides.

Certain embodiments comprise solid or semi-solid fats comprising any of the disclosed triglycerides or any combination thereof. Solid or semi-solid fats may comprise between 1-99% of disclosed heterogenous saturated triglycerides, with other components having different triglycerides.

Disclosed triglycerides may be mixed into MCT oil and/or into any type of vegetable oil (e.g., canola, soy, olive, etc.) at various proportions, e.g., 1%, 5%, 10%, 30%, 50%, 70%, 90%, 99% (w/w) or any intermediate percentage.

Certain embodiments comprise cosmetics products that include disclosed heterogenous triglyceride comprising three non-identical aliphatic saturated fatty acids. e.g., between 1% and 99% by weight. Certain embodiments comprise industrial oils and/or greases that include disclosed heterogenous triglyceride comprising three non-identical aliphatic saturated fatty acids, e.g., between 1% and 99% by weight.

In various embodiments, some antioxidants may be added to any of taste-enhanced liquid oil-based suspension 130 (e.g., to carrier oil 78), solid or semi-solid oil derivative 105 having heterogenous triglycerides and/or any other oil.

The inventors have found out that both vegetable oil with antioxidants and MCT oil oxidize during use in frying food, and therefore both types of current frying oil pose health hazards by their use in food production. Oxidation includes primary oxidation that forms hydroperoxides—the level of which being measured by the peroxide value (PV), and secondary oxidation that forms carbonyls, aldehydes and other compounds as decomposition products of the hydroperoxides—the level of which being measured by the anisidine value (AV). While hydroperoxides (expressed as PV) are the primary products in lipid oxidation, they are unstable and further decompose into many secondary compounds (expressed as AV). PV and AV are combined to yield the total oxidation value. TOTOX, defined as TOTOX=2·PV+AV, to express the overall oxidation state of the oil. The TOTOX is often used to estimate oxidative deterioration of lipids, as it has the advantage of combining the amounts of primary oxidation products (hydroperoxides) with secondary products (e.g., aldehydes, principally alkenals and alkadienals) in fats or oils.

Typical thresholds are PV=5 milliequivalents of active oxygen per kg oil, which is the primary oxidation threshold for vegetable oils used in retail as set by the American Oil Chemists' Society Official Method Cd 8-53 and also set by the Israeli national regulation, or up to PV=10 milliequivalents of active oxygen per kg oil as set by Section 2 in the Codex Standards for Fats and Oils from Vegetable Sources; and TOTOX=26 as a well-established international threshold set, e.g., as the standard for fish oils. Codex Standard 329-2017, for marine omega-3's oils (there is however no regulation concerning TOTOX of vegetable oil).

Figure 9A:
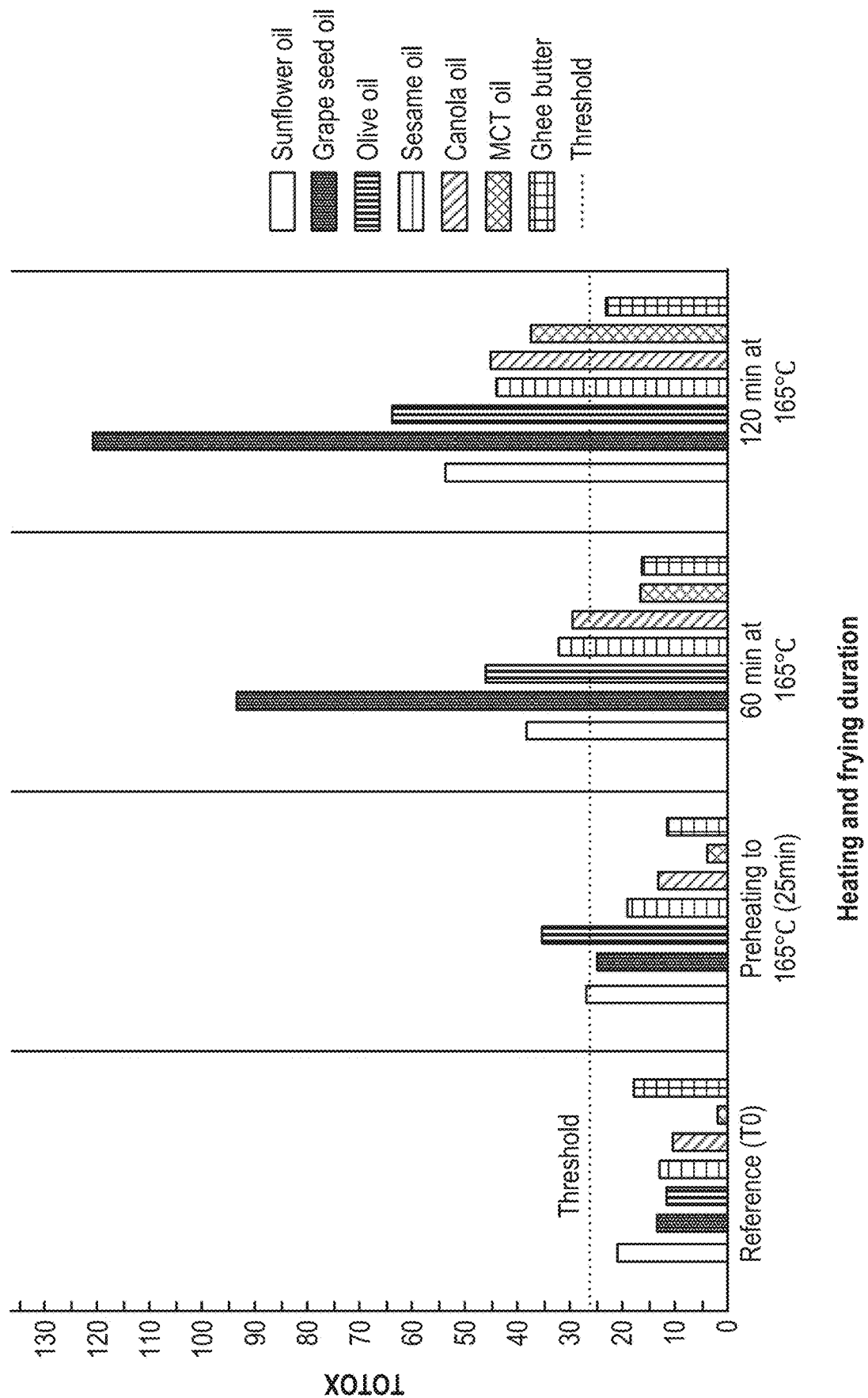
FIGS. 9A and 9B provide experimental results indicating the oxidation of both vegetable oil with antioxidants and MCT oil during frying—as used in the prior art.

FIG. 9A presents the total oxidation values measured under lab conditions for various types of frying oil over time during their use, compared to a threshold of TOTOX=26—indicating that all vegetable oils reached high TOTOX values after one hour at 165° C., and even MCT oil reached high TOTOX values after two hours at 165° C. The results specifically show that while synthetic MCT oil (including saturated fatty acids) oxidizes slower than vegetable oils (due to their high content of unsaturated fatty acids), surprisingly even MCT oil oxidizes after extended heating. It is noted that the experimental conditions did not include any addition of food that would have slowed the oxidation process, and that two hours of heating are considered excessive conditions, which nevertheless constitute common practice in the food industry.

Figure 9B:
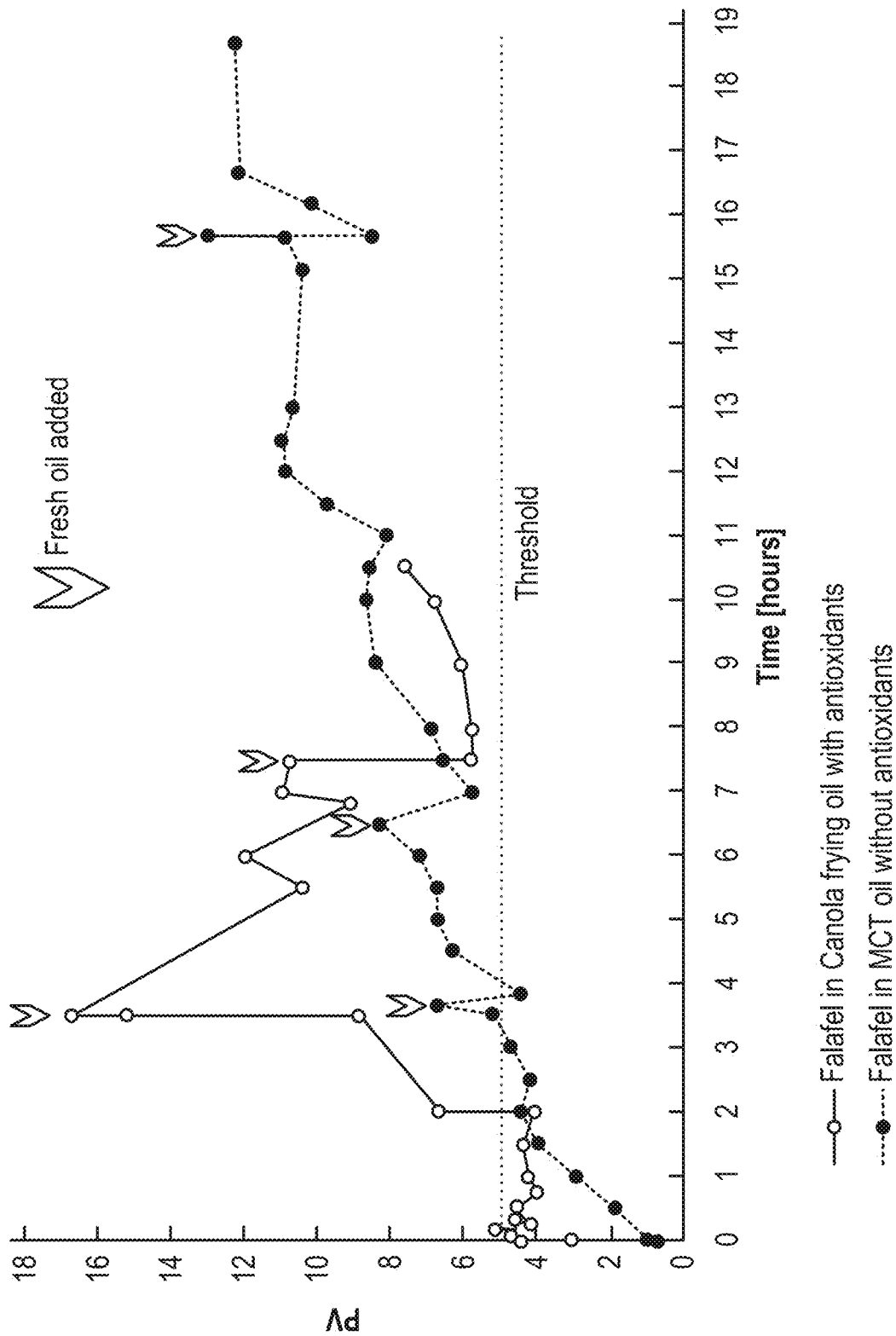

FIG. 9B presents the peroxide value (PV) measured under field conditions for frying falafel (with occasional additions of fresh oil, as commonly practiced representative conditions) in vegetable (canola) oil that includes antioxidants (specifically Brökelmann's BRÖLIO™ frying oil) and in MCT oil (60/40) without antioxidants—showing that both cross the threshold of PV=5 after several hours of use.

FIGS. 10A-10E provide experimental results indicating that disclosed oils exhibit superior resistance to oxidation, according to some embodiments of the invention. The figures indicate the unexpected need, unexpected benefits and different effects of adding antioxidants to MCT oil. Different types and concentrations of antioxidants were examined for their preservative effects. Specifically. Tocobiol® antioxidants contain 2% of green tea extract and 98% of a tocopherols blend (at least 5% a-tocopherol, at least 55% β- and γ-tocopherols, and at least 18% δ tocopherol). Tocobiol® antioxidants were examined at concentrations of 200 ppm (mg/1) and 2000 ppm—the latter representative of typical usage rates (1000 to 3000 ppm) as additives for unsaturated oils. Origanox™ OS-T antioxidants contain extracts of polyphenols (catechins) from green tea (*Camellia sinensis*) leaves (FEMA GRAS™ No. 4812). RosmaVitaol antioxidants contain Vitiva d.d.™ RosmaVitaol 4™ flavour, which is a solution of natural rosemary (*Rosmarinus officinalis*) extract in rapeseed oil.

Figure 10A:
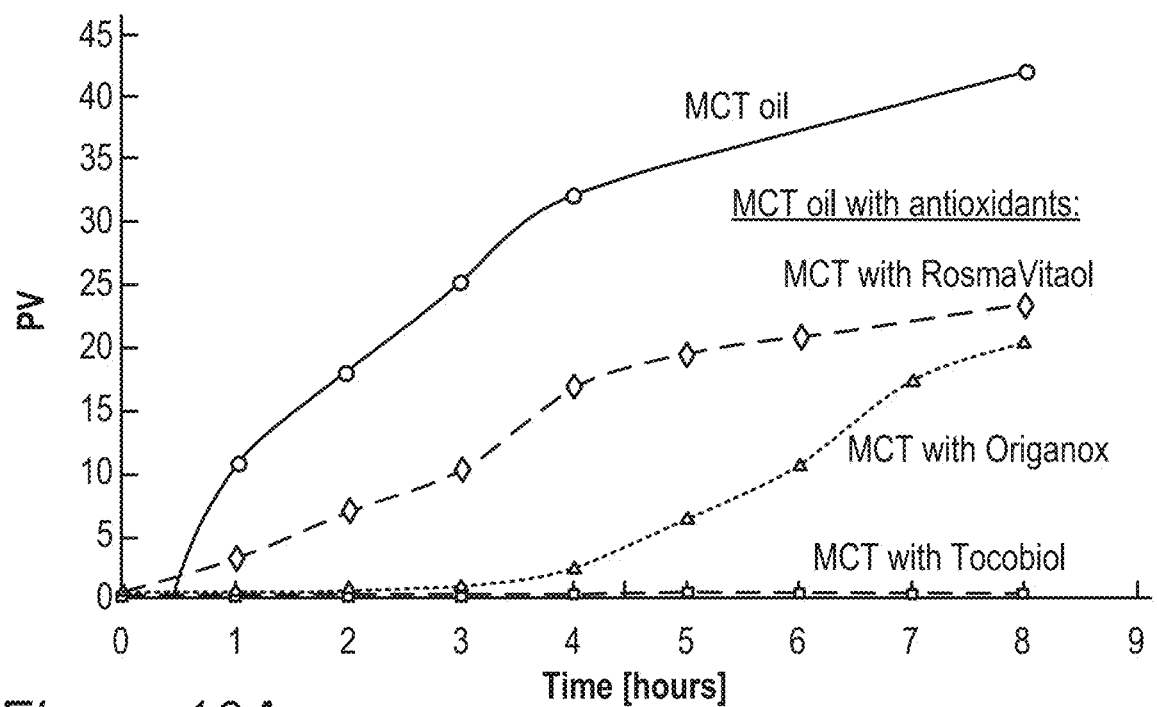
FIGS. 10A-10E provide experimental results indicating that disclosed oils exhibit superior resistance to oxidation, according to some embodiments of the invention.
Figure 10B:
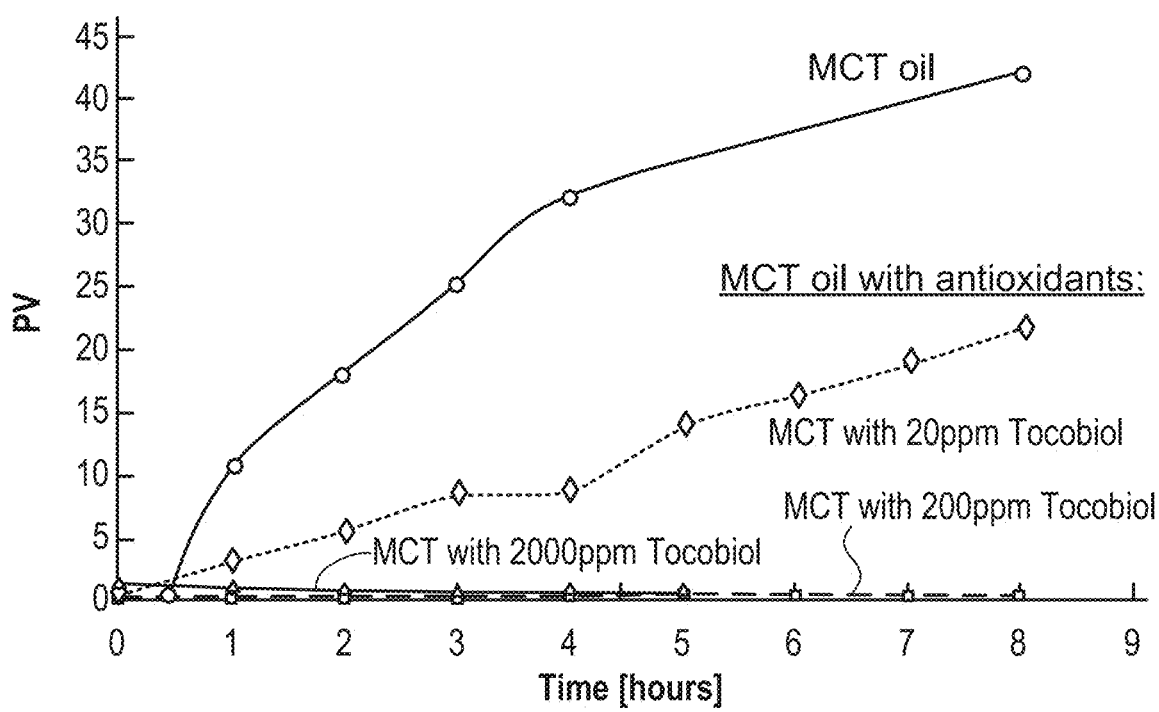

FIG. 10A provides comparative PV values over time, under lab conditions, for heating MCT oil without and with different types of antioxidants (Tocobiol®, Origanox™, RosmaVitaol). Unexpectedly, synthetic MCT oil was shown to create oxidation products after 1-2 hours of heating, and reaching high PV values during consecutive heating. In contrast, the different types of antioxidants reduced the amount of oxidation products, with Tocobiol® practically protecting the oil from oxidation, even over very long periods of heating. FIG. 10B provides comparative PV values over time, under lab conditions, for heating MCT oil without and with different concentrations of antioxidants. Although the typical usage rate of antioxidants with unsaturated oils is 1000 to 3000 ppm for different food applications the inventors have found out that for protecting MCT oil a lower optimum concentration of about 200 ppm (mg/1) is required, and that protection is achieved even at extremely low concentrations of 20 ppm. Low antioxidants concentration of 200 ppm still fully protect the MCT oil, maintaining the PV below 1, and well below the PV=5 threshold.

Figure 10C:
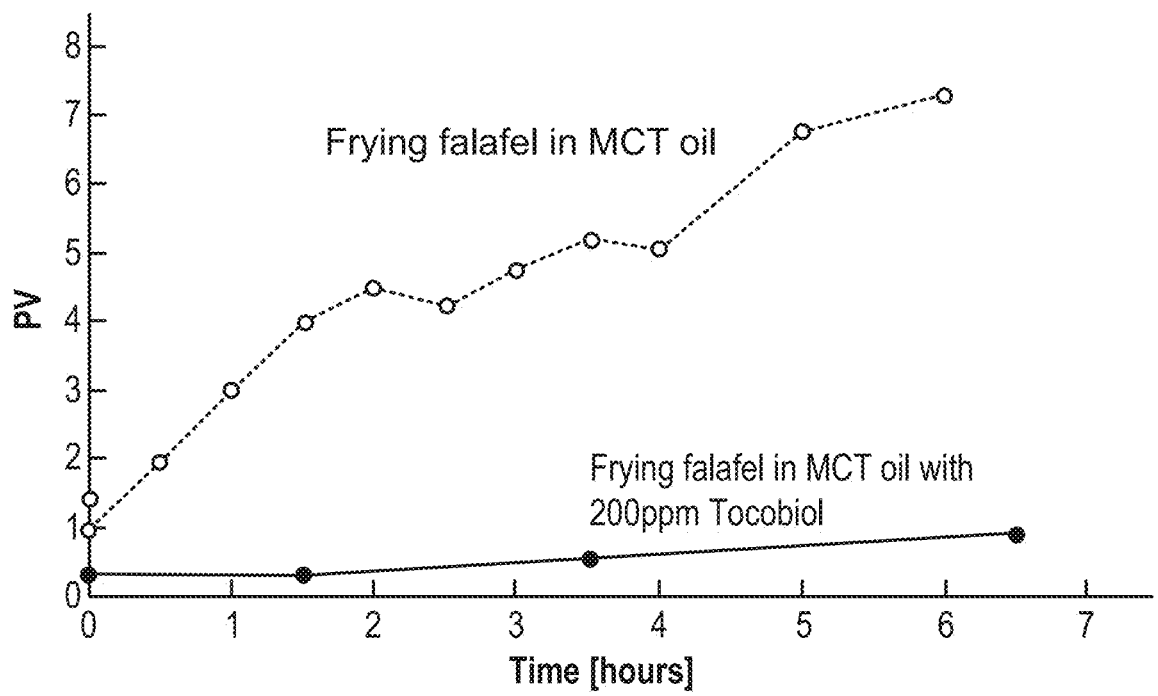

FIG. 10C provides the comparative PV index for frying falafel in MCT oil without and with antioxidants, under field conditions. Prior art MCT oil exhibits PV values larger than 5 after about three hours, while disclosed oils with antioxidants still stay at PV<1 after six hours of use.

Figure 10D:
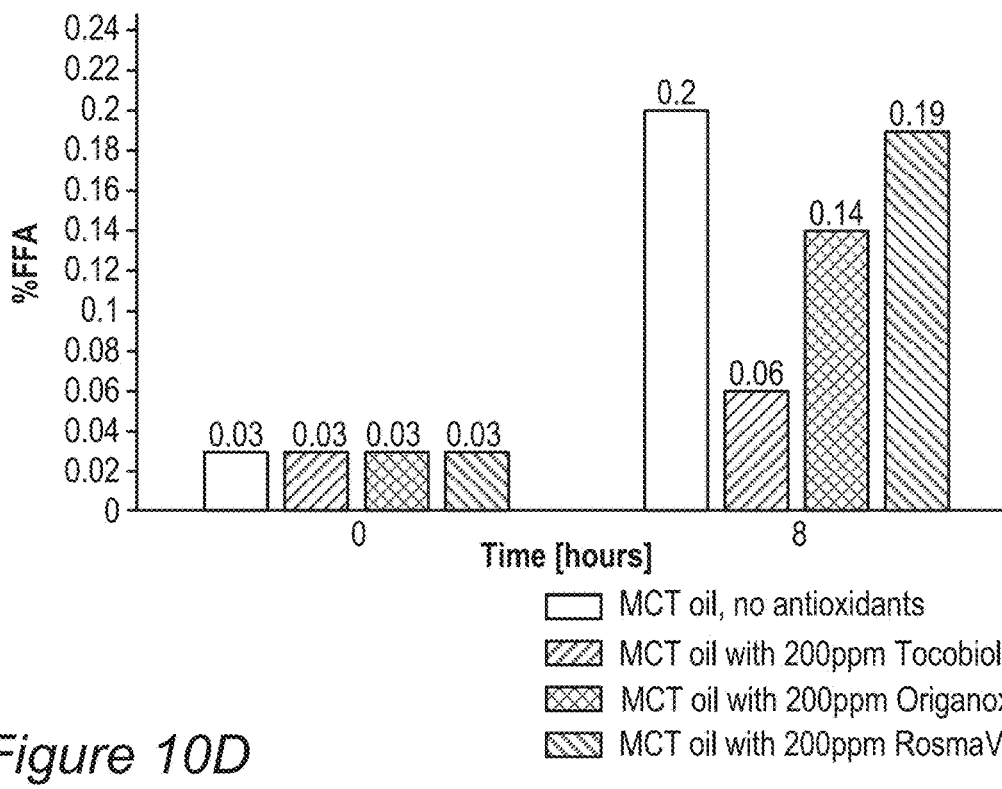
Figure 10E:
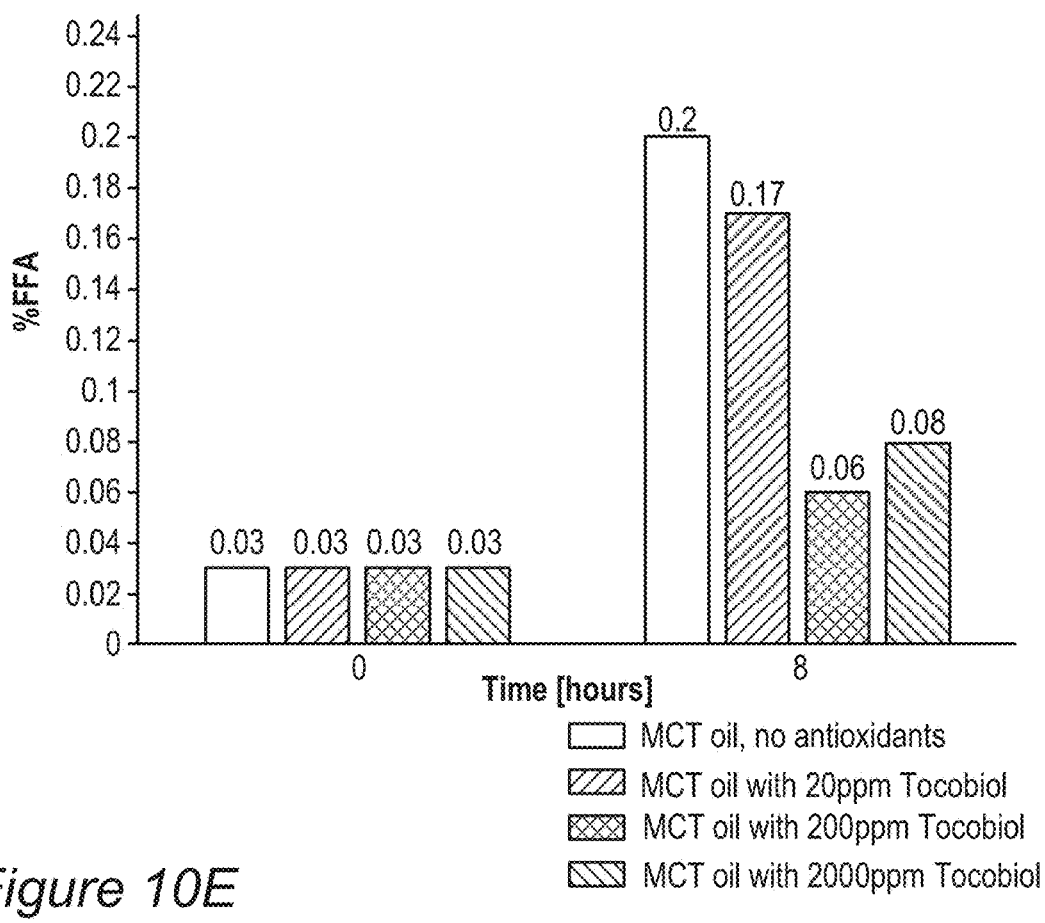

FIG. 10D provides comparative levels of free fatty acids (% FFA) after eight hours of heating MCT oil without and with different types of antioxidants—indicating decomposition of MCT oil without antioxidants as well as a correlation between the extent of decomposition and the PV values presented in FIG. 10A for the three types of antioxidants. FIG. 10E provides comparative levels of free fatty acids (% FFA) after eight hours of heating MCT oil without and with different concentrations of antioxidants—indicating decomposition of MCT oil without antioxidants as well as a correlation between the concentration of antioxidants and the prevention of oil decomposition.

It is noted that the determination of the FFA in oils and fats was carried out by a photometric measurement based on a potentiometric titration method. The result is expressed as percentage of fatty acids (mainly oleic and maleic acids).

As indicated in FIGS. 10D and 10E, in certain embodiments the most effective antioxidants as additions to MCT oil were found to be tocopherols at a concentration of about 200 ppm (mg/l), which is ten-fold lower than the average usage concentration of antioxidants to protect unsaturated oils.

Non-limiting examples for antioxidants that may be added to the oil include tocopherols (e.g., vitamin E), Carotenoids (e.g., β-carotene), synthetic compounds (e.g., butylated hydroxytoluene, BHT, butylated hydroxyanisole BHA, tert-Butylhydroquinone, TBHQ, propyl gallate, ethoxyquin), natural extracts (e.g., flavonoids, rosemary, spice extracts, tea catechins, seaweed), phospholipids, retinol (vitamin A), various acids (e.g., citric acid, phosphoric acid, ascorbic acid (vitamin C), ethylene diamine tetraacetic acid (EDTA), uric acid), or any variants or combinations thereof.

Advantageously, disclosed frying oils have increased resistance against oxidation while being used for frying. While addition of antioxidants increases the usage time of vegetable oils about five times, using disclosed frying oil that includes triglycerides with at least 98% saturated fatty acids provides a basic usage time that is still longer than vegetable oils with antioxidants, and disclosed frying oil with antioxidants has a practically unlimited duration of usage, at least ten times the usage time of vegetable oils with antioxidants.

Elements from the figures and description above may be combined in any operable combination, and the illustration of certain elements in certain figures and not in others merely serves an explanatory purpose and is non-limiting.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method preparing an oil-based suspension, the method comprising:
    mixing crystalline sucrose particles with a carrier liquid oil to yield a mixture consisting of the crystalline sucrose particles in carrier liquid oil, and
    reducing a particle size of the crystalline sucrose particles within the carrier liquid oil in the mixture in at least two steps comprising:
        a first reduction step to a median particle size of between 50-150 μm, and
        a second reduction step to a median particle size of between 0.1-15 μm to yield a taste-enhanced liquid oil-based suspension consisting of the carrier liquid oil and crystalline sucrose particles having median diameter of between 0.1 μm and 15 μm,
    wherein both reduction steps are carried out on the particles within the carrier liquid oil,
    wherein the first reduction step is carried out by high shear mechanical mixing and the second reduction step is carried out by high-pressure high-shear microfluidizing and/or ball milling; and
    wherein the taste-enhanced liquid oil-based suspension provides enhanced sweetening relative to a composition comprising the same weight percentage of sucrose particles not subjected to two particle size reduction steps.

2. The method of claim 1, further comprising adding the taste-enhanced liquid oil-based suspension to a food product.

3. The method of claim 1, further comprising mixing the oil-based suspension with an additional oil or product with a high-oil content, to provide a final sweetened product.

4. The method of claim 1, further comprising concentrating the oil-based suspension to increase a concentration of the crystalline sucrose particles and a viscosity of the oil-based suspension.

5. The method of claim 1, further configured to reduce the particle size of the crystalline sucrose to have a median diameter of between 0.1 μm and 5 μm.

6. The method of claim 1, further configured to yield the mixture having between 1% and 30% w/w of the crystalline sucrose particles.

7. The method of claim 1, wherein the carrier liquid oil comprises at least one of: medium chain triglyceride (MCT) oil, canola oil, coconut oil, peanut butter oil, palm oil, olive oil, fish oil, sunflower seed oil, soy oil, or any combination thereof.

8. The method of claim 1, wherein the carrier liquid oil comprises, at least partly, at least one heterogenous triglyceride comprising three non-identical aliphatic saturated fatty acids that include at least one fatty acid with more than ten carbon atoms.

9. The method of claim 8, wherein the carrier liquid oil consists of MCT oil and/or the at least one heterogenous triglyceride.

10. The method of claim 1, wherein, after the at least two reduction steps, at least 90% of the particles have a particle size that is smaller than 20 μm.

* * * * *